(12) United States Patent
Self et al.

(10) Patent No.: US 10,619,254 B2
(45) Date of Patent: *Apr. 14, 2020

(54) ELECTROCHEMICAL, CHLORINATION, AND OXYCHLORINATION SYSTEMS AND METHODS TO FORM PROPYLENE OXIDE OR ETHYLENE OXIDE

(71) Applicant: Calera Corporation, Moss Landing, CA (US)

(72) Inventors: Kyle Self, San Jose, CA (US); Michael Joseph Weiss, Los Gatos, CA (US); Ryan J Gilliam, San Jose, CA (US); Thomas Albrecht, Sunnyvale, CA (US); Gal Mariansky, Morgan Hill, CA (US)

(73) Assignee: Calera Corporation, Moss Landing, CA (US)

( * ) Notice: Subject to any disclaimer, the term of this patent is extended or adjusted under 35 U.S.C. 154(b) by 167 days.

This patent is subject to a terminal disclaimer.

(21) Appl. No.: 15/963,637

(22) Filed: Apr. 26, 2018

(65) Prior Publication Data

US 2018/0245223 A1    Aug. 30, 2018

Related U.S. Application Data

(63) Continuation-in-part of application No. 15/338,235, filed on Oct. 28, 2016, now Pat. No. 10,266,954.

(Continued)

(51) Int. Cl.
*C25B 3/06* (2006.01)
*C07D 301/24* (2006.01)
(Continued)

(52) U.S. Cl.
CPC ............... *C25B 3/06* (2013.01); *C07C 17/08* (2013.01); *C07C 29/64* (2013.01); *C07C 31/36* (2013.01);
(Continued)

(58) Field of Classification Search
CPC ........... C25B 3/06; C07C 17/08; C07C 31/36; C07D 303/04; C07D 29/64; C07D 301/24
See application file for complete search history.

(56) References Cited

U.S. PATENT DOCUMENTS 2,752,402 A   6/1956  Pye
2,792,342 A   5/1957  Tuwiner
(Continued)

FOREIGN PATENT DOCUMENTS

CA    1339833 C     4/1998
CN    103238233 B   9/2015
(Continued)

OTHER PUBLICATIONS

Acquah, et al. The electrochlorination of aliphatic hydrocarbons. J. Appl. Chem. Biotechnol. 1972; 22:1195-1200.
(Continued)

*Primary Examiner* — Louis J Rufo
(74) *Attorney, Agent, or Firm* — Calera Corporation; Vandana Bansal

(57) ABSTRACT

Disclosed herein are methods and systems that relate to various configurations of electrochemical oxidation, chlorine oxidation, oxychlorination, chlorination, and epoxidation reactions to form propylene oxide or ethylene oxide.

16 Claims, 12 Drawing Sheets

Related U.S. Application Data

(60) Provisional application No. 62/490,903, filed on Apr. 27, 2017, provisional application No. 62/528,273, filed on Jul. 3, 2017, provisional application No. 62/595,389, filed on Dec. 6, 2017.

(51) Int. Cl.
*C07C 31/36* (2006.01)
*C07C 29/64* (2006.01)
*C07D 303/04* (2006.01)
*C07C 17/08* (2006.01)

(52) U.S. Cl.
CPC ......... *C07D 301/24* (2013.01); *C07D 303/04* (2013.01)

(56) References Cited

U.S. PATENT DOCUMENTS

| | | |
|---|---|---|
| 2,999,887 A | 9/1961 | Finlay |
| 3,079,444 A | 2/1963 | Jacobowsky et al. |
| 3,214,481 A | 10/1965 | Heinemann et al. |
| 3,214,482 A | 10/1965 | Caropreso et al. |
| 3,277,189 A | 10/1966 | Bromberg |
| 3,345,144 A | 10/1967 | Klopfer et al. |
| 3,397,226 A | 8/1968 | Fenton |
| 3,427,235 A | 2/1969 | Joseph |
| 3,437,712 A | 4/1969 | Robert et al. |
| 3,461,180 A | 8/1969 | Heinz et al. |
| 3,510,532 A | 5/1970 | Frank et al. |
| 3,607,420 A | 9/1971 | Cutler |
| 3,634,330 A | 1/1972 | Max et al. |
| 3,635,803 A | 1/1972 | Binns et al. |
| 3,691,239 A | 9/1972 | Homer et al. |
| 3,723,544 A | 3/1973 | Roberts, Jr. |
| 3,884,984 A | 5/1975 | Hirose et al. |
| 3,985,794 A | 10/1976 | Calcagno et al. |
| 4,008,133 A | 2/1977 | Gelbein et al. |
| 4,108,752 A | 8/1978 | Pohto et al. |
| 4,111,779 A | 9/1978 | Seko et al. |
| 4,126,526 A | 11/1978 | Kwon et al. |
| 4,190,508 A | 2/1980 | Kametani et al. |
| 4,256,719 A | 3/1981 | Van Andel |
| 4,277,405 A | 7/1981 | Apanel |
| 4,319,977 A | 3/1982 | Wortley |
| 4,324,625 A | 4/1982 | Cumbo |
| 4,376,019 A | 3/1983 | Gamlen et al. |
| 4,379,019 A | 4/1983 | Pool |
| 4,394,227 A | 7/1983 | Jaeger et al. |
| 4,402,811 A | 9/1983 | Klotz et al. |
| 4,555,317 A | 11/1985 | Nicolas et al. |
| 4,581,116 A | 4/1986 | Plowman et al. |
| 4,595,469 A | 6/1986 | Foller |
| 4,634,506 A | 1/1987 | Novak et al. |
| 4,643,818 A | 2/1987 | Seko et al. |
| 4,672,142 A | 6/1987 | Hundeck et al. |
| 4,726,887 A | 2/1988 | McIntyre |
| 4,767,519 A | 8/1988 | De Nora |
| 4,814,420 A | 3/1989 | Brunelle et al. |
| 4,834,847 A | 5/1989 | McIntyre |
| 4,908,198 A | 3/1990 | Weinberg |
| 4,950,268 A | 8/1990 | Rink |
| 4,950,368 A | 8/1990 | Weinberg et al. |
| 5,050,603 A | 9/1991 | Stokes et al. |
| 5,296,107 A | 3/1994 | Harrison |
| 5,364,508 A | 11/1994 | Weres et al. |
| 5,437,771 A | 8/1995 | Shimamune et al. |
| 5,523,425 A | 6/1996 | Pech et al. |
| 5,532,389 A * | 7/1996 | Trent ............... C01B 11/04 549/522 |
| 5,595,641 A | 1/1997 | Traini et al. |
| 5,891,318 A | 4/1999 | Freire et al. |
| 5,932,750 A | 8/1999 | Hayashi et al. |
| 6,043,400 A | 3/2000 | Jorge |
| 6,117,286 A | 9/2000 | Shimamune et al. |
| 6,146,787 A | 11/2000 | Harrup et al. |
| 6,368,473 B1 | 4/2002 | Furuya et al. |
| 6,372,102 B1 | 4/2002 | Sakata et al. |
| 6,383,349 B1 | 5/2002 | Sakata et al. |
| 6,395,153 B1 | 5/2002 | Matousek et al. |
| 6,591,199 B2 | 7/2003 | Tremblay et al. |
| 7,157,609 B2 | 1/2007 | Tanaka et al. |
| 7,404,878 B2 | 7/2008 | Katayama et al. |
| 7,569,083 B2 | 8/2009 | Katayama et al. |
| 7,616,006 B2 | 11/2009 | Tremblay et al. |
| 7,658,835 B2 | 2/2010 | Gestermann et al. |
| 7,708,867 B2 | 5/2010 | Yamada et al. |
| 7,735,274 B2 | 6/2010 | Constantz et al. |
| 7,744,761 B2 | 6/2010 | Constantz et al. |
| 7,749,476 B2 | 7/2010 | Constantz et al. |
| 7,753,618 B2 | 7/2010 | Constantz et al. |
| 7,754,169 B2 | 7/2010 | Constantz et al. |
| 7,771,684 B2 | 8/2010 | Constantz et al. |
| 7,790,012 B2 | 9/2010 | Kirk et al. |
| 7,797,137 B2 | 9/2010 | Veillette et al. |
| 7,815,880 B2 | 10/2010 | Constantz et al. |
| 7,818,276 B2 | 10/2010 | Veillette et al. |
| 7,829,053 B2 | 11/2010 | Constantz et al. |
| 7,837,842 B1 | 11/2010 | Mayers, Sr. et al. |
| 7,875,163 B2 | 1/2011 | Gilliam et al. |
| 7,887,694 B2 | 2/2011 | Constantz et al. |
| 7,906,028 B2 | 3/2011 | Constantz et al. |
| 7,914,652 B2 | 3/2011 | Yamada et al. |
| 7,914,685 B2 | 3/2011 | Constantz et al. |
| 7,922,809 B1 | 4/2011 | Constantz et al. |
| 7,931,809 B2 | 4/2011 | Constantz et al. |
| 7,933,511 B2 | 4/2011 | Masuki |
| 7,939,336 B2 | 5/2011 | Constantz et al. |
| 7,966,250 B2 | 6/2011 | Constantz et al. |
| 7,993,500 B2 | 8/2011 | Gilliam et al. |
| 7,993,511 B2 | 8/2011 | Gilliam et al. |
| 8,006,446 B2 | 8/2011 | Constantz et al. |
| 8,062,418 B2 | 11/2011 | Constantz et al. |
| 8,114,214 B2 | 2/2012 | Constantz et al. |
| 8,114,265 B2 | 2/2012 | Berriah et al. |
| 8,137,455 B1 | 3/2012 | Constantz et al. |
| 8,152,987 B2 | 4/2012 | Tremblay et al. |
| 8,197,649 B2 | 6/2012 | Saiki et al. |
| 8,357,270 B2 | 1/2013 | Gilliam et al. |
| 8,894,830 B2 | 11/2014 | Gilliam et al. |
| 8,940,139 B2 | 1/2015 | Asaumi et al. |
| 9,108,844 B2 | 8/2015 | Huss |
| 9,175,410 B2 | 11/2015 | Izawa et al. |
| 9,181,624 B2 | 11/2015 | Sugiyama et al. |
| 9,187,834 B2 | 11/2015 | Albrecht et al. |
| 9,187,835 B2 | 11/2015 | Albrecht et al. |
| 9,200,375 B2 | 12/2015 | Gilliam et al. |
| 9,273,404 B2 | 3/2016 | Bulan et al. |
| 9,828,313 B2 | 11/2017 | Weiss et al. |
| 9,957,621 B2 | 5/2018 | Albrecht et al. |
| 9,957,623 B2 | 5/2018 | Gilliam et al. |
| 2003/0150819 A1 | 8/2003 | Iseki et al. |
| 2004/0251199 A1 | 12/2004 | Benavides |
| 2004/0267063 A1 | 12/2004 | Harth et al. |
| 2005/0244689 A1 | 11/2005 | Horiguchi et al. |
| 2006/0124445 A1 | 6/2006 | Labrecque et al. |
| 2006/0149102 A1 | 7/2006 | Voight et al. |
| 2007/0014709 A1 | 1/2007 | Moyes et al. |
| 2007/0292762 A1 | 12/2007 | Johnson |
| 2008/0023339 A1 | 1/2008 | Berggren et al. |
| 2008/0029404 A1 | 2/2008 | Weber et al. |
| 2008/0223727 A1 | 9/2008 | Oloman et al. |
| 2008/0275279 A1 | 11/2008 | Podkolzin et al. |
| 2009/0001020 A1 | 1/2009 | Constantz et al. |
| 2009/0020044 A1 | 1/2009 | Constantz et al. |
| 2009/0029199 A1 | 1/2009 | Tao |
| 2009/0087698 A1 | 4/2009 | Huth et al. |
| 2009/0169452 A1 | 7/2009 | Constantz et al. |
| 2009/0202410 A1 | 8/2009 | Kawatra et al. |
| 2009/0301352 A1 | 12/2009 | Constantz et al. |
| 2009/0325031 A1 | 12/2009 | Sugawara et al. |
| 2010/0000444 A1 | 1/2010 | Constantz et al. |
| 2010/0024686 A1 | 2/2010 | Constantz et al. |
| 2010/0032347 A1 | 2/2010 | Ring et al. |

(56) References Cited

U.S. PATENT DOCUMENTS

| | | |
|---|---|---|
| 2010/0041927 A1 | 2/2010 | Olver et al. |
| 2010/0051469 A1 | 3/2010 | Stolberg |
| 2010/0051859 A1 | 3/2010 | House et al. |
| 2010/0063902 A1 | 3/2010 | Constantz et al. |
| 2010/0077691 A1 | 4/2010 | Constantz et al. |
| 2010/0077922 A1 | 4/2010 | Constantz et al. |
| 2010/0083880 A1 | 4/2010 | Constantz et al. |
| 2010/0084280 A1 | 4/2010 | Gilliam et al. |
| 2010/0108537 A1 | 5/2010 | Perego et al. |
| 2010/0111810 A1 | 5/2010 | Constantz et al. |
| 2010/0116683 A1 | 5/2010 | Gilliam et al. |
| 2010/0132556 A1 | 6/2010 | Constantz et al. |
| 2010/0132591 A1 | 6/2010 | Constantz et al. |
| 2010/0135865 A1 | 6/2010 | Constantz et al. |
| 2010/0135882 A1 | 6/2010 | Constantz et al. |
| 2010/0140103 A1 | 6/2010 | Gilliam et al. |
| 2010/0144521 A1 | 6/2010 | Constantz et al. |
| 2010/0150802 A1 | 6/2010 | Gilliam et al. |
| 2010/0154679 A1 | 6/2010 | Constantz et al. |
| 2010/0155258 A1 | 6/2010 | Kirk et al. |
| 2010/0158786 A1 | 6/2010 | Constantz et al. |
| 2010/0170805 A1 | 7/2010 | Krafft et al. |
| 2010/0179302 A1 | 7/2010 | Krafft et al. |
| 2010/0196104 A1 | 8/2010 | Constantz et al. |
| 2010/0200419 A1 | 8/2010 | Gilliam et al. |
| 2010/0219373 A1 | 9/2010 | Seeker et al. |
| 2010/0224503 A1 | 9/2010 | Kirk et al. |
| 2010/0229725 A1 | 9/2010 | Farsad et al. |
| 2010/0230293 A1 | 9/2010 | Gilliam et al. |
| 2010/0230830 A1 | 9/2010 | Farsad et al. |
| 2010/0236242 A1 | 9/2010 | Farsad et al. |
| 2010/0239467 A1 | 9/2010 | Constantz et al. |
| 2010/0239487 A1 | 9/2010 | Constantz et al. |
| 2010/0247410 A1 | 9/2010 | Constantz et al. |
| 2010/0258035 A1 | 10/2010 | Constantz et al. |
| 2010/0258450 A1 | 10/2010 | Burtch |
| 2010/0258506 A1 | 10/2010 | Berkowitz et al. |
| 2010/0270167 A1 | 10/2010 | McFarland |
| 2010/0276299 A1 | 11/2010 | Kelly et al. |
| 2010/0290967 A1 | 11/2010 | Detournay et al. |
| 2010/0313793 A1 | 12/2010 | Constantz et al. |
| 2010/0313794 A1 | 12/2010 | Constantz et al. |
| 2010/0319586 A1 | 12/2010 | Blount et al. |
| 2010/0326328 A1 | 12/2010 | Constantz et al. |
| 2011/0005938 A1 | 1/2011 | Wolf et al. |
| 2011/0028765 A1 | 2/2011 | Mehta |
| 2011/0030586 A1 | 2/2011 | Constantz et al. |
| 2011/0030957 A1 | 2/2011 | Constantz et al. |
| 2011/0033239 A1 | 2/2011 | Constantz et al. |
| 2011/0035154 A1 | 2/2011 | Kendall et al. |
| 2011/0036728 A1 | 2/2011 | Farsad |
| 2011/0042230 A1 | 2/2011 | Gilliam et al. |
| 2011/0054084 A1 | 3/2011 | Constantz et al. |
| 2011/0059000 A1 | 3/2011 | Constantz et al. |
| 2011/0067600 A1 | 3/2011 | Constantz et al. |
| 2011/0067603 A1 | 3/2011 | Constantz et al. |
| 2011/0067605 A1 | 3/2011 | Constantz et al. |
| 2011/0071309 A1 | 3/2011 | Constantz et al. |
| 2011/0076587 A1 | 3/2011 | Wang et al. |
| 2011/0079515 A1 | 4/2011 | Gilliam et al. |
| 2011/0081585 A1 | 4/2011 | Montgomery |
| 2011/0083968 A1 | 4/2011 | Gilliam et al. |
| 2011/0091366 A1 | 4/2011 | Kendall et al. |
| 2011/0091955 A1 | 4/2011 | Constantz et al. |
| 2011/0120888 A1 | 5/2011 | James et al. |
| 2011/0132234 A1 | 6/2011 | Constantz et al. |
| 2011/0147227 A1 | 6/2011 | Gilliam et al. |
| 2011/0152580 A1 | 6/2011 | Hook et al. |
| 2011/0203489 A1 | 8/2011 | Constantz et al. |
| 2011/0226989 A9 | 9/2011 | Seeker et al. |
| 2011/0240916 A1 | 10/2011 | Constantz et al. |
| 2011/0247336 A9 | 10/2011 | Farsad et al. |
| 2011/0269990 A1 | 11/2011 | Honda et al. |
| 2011/0277474 A1 | 11/2011 | Constantz et al. |
| 2011/0277670 A1 | 11/2011 | Self et al. |
| 2011/0315561 A1 | 12/2011 | Rabaey et al. |
| 2012/0000789 A1 | 1/2012 | Turek et al. |
| 2012/0003125 A1 | 1/2012 | Madokoro et al. |
| 2012/0152804 A1 | 6/2012 | Koseoglu et al. |
| 2012/0292196 A1* | 11/2012 | Albrecht ............ C25B 1/00 205/351 |
| 2012/0292197 A1 | 11/2012 | Albrecht et al. |
| 2013/0206606 A1 | 8/2013 | Gilliam et al. |
| 2013/0240372 A1 | 9/2013 | Bulan et al. |
| 2014/0353146 A1 | 12/2014 | Gilliam et al. |
| 2015/0038750 A1 | 2/2015 | Weiss et al. |
| 2015/0337443 A1 | 11/2015 | Albrecht et al. |
| 2015/0361564 A1 | 12/2015 | Albrecht et al. |
| 2016/0040304 A1 | 2/2016 | Albrecht et al. |
| 2016/0060774 A1 | 3/2016 | Gilliam et al. |
| 2016/0076156 A1 | 3/2016 | Albrecht et al. |
| 2016/0108529 A1 | 4/2016 | Albrecht et al. |
| 2016/0230291 A1 | 8/2016 | Albrecht et al. |
| 2017/0073823 A1 | 3/2017 | Albrecht et al. |
| 2017/0121832 A1 | 5/2017 | Albrecht et al. |
| 2018/0044267 A1 | 2/2018 | Weiss et al. |
| 2018/0347056 A1 | 12/2018 | Self et al. |
| 2019/0203365 A1 | 7/2019 | Albrecht et al. |

FOREIGN PATENT DOCUMENTS

| | | |
|---|---|---|
| DE | 19614683 A1 | 10/1997 |
| EP | 0039547 A1 | 11/1981 |
| EP | 0039547 B1 | 7/1984 |
| EP | 1362133 A1 | 11/2003 |
| EP | 2253600 A1 | 11/2010 |
| EP | 1362133 B1 | 7/2011 |
| EP | 2697410 B1 | 6/2015 |
| FR | 1539499 A | 9/1968 |
| GB | 812680 A | 4/1959 |
| GB | 1019437 A | 2/1966 |
| GB | 1063175 A | 3/1967 |
| GB | 1063283 A | 3/1967 |
| GB | 1063284 A | 3/1967 |
| GB | 1553819 A | 10/1979 |
| JP | S56169631 A | 12/1981 |
| JP | S5727129 A | 2/1982 |
| JP | S5874624 A | 5/1983 |
| JP | S63293186 A | 11/1988 |
| JP | H0238573 B2 | 8/1990 |
| JP | H0356683 A | 3/1991 |
| JP | H046290 A | 1/1992 |
| JP | H0432594 A | 2/1992 |
| JP | H05214573 A | 8/1993 |
| JP | H1081986 A | 3/1998 |
| JP | H11256385 A | 9/1999 |
| JP | 2000199093 A | 7/2000 |
| JP | 2001262387 A | 9/2001 |
| JP | 2004027267 A | 1/2004 |
| JP | 2005511670 A | 4/2005 |
| JP | 2009299111 A | 12/2009 |
| TW | 201313958 A | 4/2013 |
| WO | WO-2004097073 A1 | 11/2004 |
| WO | WO-2007058472 A1 | 5/2007 |
| WO | WO-2008018928 A2 | 2/2008 |
| WO | WO-2008148055 A1 | 12/2008 |
| WO | WO-2009006295 A2 | 1/2009 |
| WO | WO-2009086460 A1 | 7/2009 |
| WO | WO-2009146436 A1 | 12/2009 |
| WO | WO-2009155378 A1 | 12/2009 |
| WO | WO-2010006242 A1 | 1/2010 |
| WO | WO-2010008896 A1 | 1/2010 |
| WO | WO-2010009273 A1 | 1/2010 |
| WO | WO-2010030826 A1 | 3/2010 |
| WO | WO-2010039903 A1 | 4/2010 |
| WO | WO-2010039909 A1 | 4/2010 |
| WO | WO-2010048457 A1 | 4/2010 |
| WO | WO-2010051458 A1 | 5/2010 |
| WO | WO-2010055152 A1 | 5/2010 |
| WO | WO-2010068924 A1 | 6/2010 |
| WO | WO-2010074686 A1 | 7/2010 |
| WO | WO-2010074687 A1 | 7/2010 |
| WO | WO-2010087823 A1 | 8/2010 |
| WO | WO-2010091029 A1 | 8/2010 |

(56) References Cited

FOREIGN PATENT DOCUMENTS

| | | |
|---|---|---|
| WO | WO-2010093713 A1 | 8/2010 |
| WO | WO-2010093716 A1 | 8/2010 |
| WO | WO-2010101953 A1 | 9/2010 |
| WO | WO-2010104989 A1 | 9/2010 |
| WO | WO-2010132863 A1 | 11/2010 |
| WO | WO-2010136744 A1 | 12/2010 |
| WO | WO-2011008223 A1 | 1/2011 |
| WO | WO-2011017609 A1 | 2/2011 |
| WO | WO-2011038076 A1 | 3/2011 |
| WO | WO-2011049996 A1 | 4/2011 |
| WO | WO-2011066293 A1 | 6/2011 |
| WO | WO-2011073621 A1 | 6/2011 |
| WO | WO-2011075680 A1 | 6/2011 |
| WO | WO-2011081681 A1 | 7/2011 |
| WO | WO-2011097468 A2 | 8/2011 |
| WO | WO-2011102868 A1 | 8/2011 |
| WO | WO-2011116236 A2 | 9/2011 |
| WO | WO-2012158969 A1 | 11/2012 |
| WO | WO-2013082811 A1 | 6/2013 |
| WO | WO-2013148216 A1 | 10/2013 |
| WO | WO-2015017585 A1 | 2/2015 |
| WO | WO-2018200785 A1 | 11/2018 |

OTHER PUBLICATIONS

Andersson, et al. High power diode laser cladding. Fabricating and Metalworking. Mar. 2014; 24-26.

Benadda, B. et al. 1996. A study of Oxygen Absorption Kinetics in Ionic Cu(I) Aqueous Solutions. Chem. Eng. Technol. 19: 34-38.

Brugger, et al. Complexation of metal ions in brines: application of electronic spectroscopy in the study of the Cu(II)—LiCl—H2O system between 25 and 90° C. Geochimica et Cosmochimica Acta. 2001; 65(16):2691-2708.

Catalytical Associates, Inc. Selective Oxychlorination of Hydrocarbons: A Critical Analysis. Oct. 1982, pp. 15-20.

Constantz, B. "The Risk of Implementing New Regulations on Game-Changing Technology: Sequestering CO2 in the Built Environment" AGU, Sep. 2009; 90(22), Jt. Assem, Suppl., Abstract.

Co-pending U.S. Appl. No. 15/338,235, filed Oct. 28, 2016.

Yuan, et al. Direct Electrochemical Synthesis and Crystal Structure of a Copper(II) Complex with a Chiral (S)-2-(diphenylmethanol-1-(2-pyridylmethyl)pyrrolidine. Inorganic Chemistry Communications (no month, 2005), vol. 8, pp. 1014-1017.

European search report and opinion dated Feb. 25, 2015 for EP Application No. 12785945.2.

European search report and opinion dated May 11, 2015 for EP Application No. 13769321.4.

"European search report with opinion dated Dec. 8, 2016 for EP14832631.7".

"European search report with written opinion dated Feb. 17, 2017 for EP16188593.4".

European search report with written opinion dated Jul. 18, 2017 for EP17150726.

Friend, L. et al. 1974. Liquid-Phase Oxychlorination of Ethylene to Produce Vinyl Chloride. Homogeneous Catalysis. American Chemical Society. Piscataway, N.J. pp. 168-176.

Georgiadou, M. et al. 1998. Modelling of copper etching in aerated chloride solutions. Journal of Applied Electrochemistry. 28: 127-134.

Hine, F. et al. 1970. Mechanism of Oxidation of Cuprous Ion in Hydrochloric Acid Solution by Oxygen. Electrochimica Acta. 15: 769-781.

International search report and written opinion dated May 23, 2013 for PCT/US2013/031064.

International search report and written opinion dated Aug. 14, 2012 for PCT/US2012/038438.

International search report and written opinion dated Oct. 15, 2014 for PCT/US2014/048976.

International search report and written opinion dated Dec. 17, 2015 for PCT/US2015/050196.

"International search report with written opinion dated Jan. 24, 2017 for PCT/US16/59455".

Jhaveri, A.S., et al. 1967. Kinetics of absorption of oxygen in aqueous solutions of cuprous chloride. Chemical Engineering Science. 22: 1-6.

Kinoshita, et al. Mass-Transfer Study of Carbon Felt, Flow-Through Electrode. J. Electrochem. Soc. 1982; 129(9):1993-1997.

Kotora, et al. Selective Additions of Polyhalognated Compounds to Chloro Substituted Ethenes Catalyzed by a Copper Complex. React. Kinet. Catal. Lett. (no month, 1991), vol. 44, No. 2, pp. 415-419.

Krishnamoorthy, et al. Chlorination of substituted aromatics on graphite anode. Asian Journal of Chemistry. 2002; 14(3-4):1801-1803.

Langer, et al. Electrogenerative and Voltameiotic Processes. Ind. Eng. Chem. Process Des. Dev. 1979; 18(4):567-579.

Langer, et al. Electrogenerative Chlorination J. Electrochem. Soc. 1970; 117(4):510-511.

Little, et al. A microstructural study of a supported liquid phase oxychlorination catalyst. Journal of Catalysis 93.1 (1985): 23-29.

Liu, et al. A spectrophotometric study of aqueouscopper(I)-chloride complexes in LiCl solutions between 100° C and 250° C. Geochimica et Cosmochimica Acta. 2002; 66(20):3615-3633.

Logager, et al. Oxidation of Ferrous Ions by Ozone in Acidic Solutions. Inorg. Chem. 1992; 31:3523-3529.

Lundstrom, et al Redox potential characteristics of cupric chloride solutions. Hydrometallurgy. 2009; 95:285-289.

Margraf, et al. Copper(II) PMDTA and Copper(II) TMEDA Complexes: Precursors for the Synthesis of Dinuclear Copper(II) Complexes. Inorgancia Chimica Acta (no month, 2005), vol. 358, pp. 1193-1203.

Muddada, et al. Ethylene oxychlorination catalysis: role of metal promoters on activity and selectivity of the process. Department of Chemistry. University of Oslo. Available at https://www.sintef.no/globalassets/project/trondheim_gts/presentasjoner/ethylene-oxychlorination-catalysis---role-of-metal-promoters-on-activity-and-selectivity-of-the-process.pdf. Nov. 3, 2011. Accessed Jan. 17, 2017.

Notice of allowance dated Feb. 12, 2018 for U.S. Appl. No. 15/341,260.

Notice of allowance dated Mar. 7, 2018 for U.S. Appl. No. 14/919,281.

Notice of allowance dated Mar. 16, 2018 for U.S. Appl. No. 14/855,262.

Notice of allowance dated Sep. 16, 2015 for U.S. Appl. No. 13/474,599.

Notice of allowance dated Sep. 28, 2017 for U.S. Appl. No. 14/446,791.

Notice of allowance dated Sep. 30, 2015 for U.S. Appl. No. 13/474,598.

Notice of allowance dated Oct. 9, 2015 for U.S. Appl. No. 13/799,131.

Office action dated Feb. 5, 2018 for U.S. Appl. No. 14/855,262.

Office action dated Feb. 8, 2018 for U.S. Appl. No. 14/834,151.

"Office action dated Feb. 9, 2017 for U.S. Appl. No. 14/446,791".

Office action dated Feb. 15, 2018 for U.S. Appl. No. 14/876,760.

Office action dated Mar. 2, 2018 for U.S. Appl. No. 14/814,935.

Office action dated Mar. 4, 2015 for U.S. Appl. No. 13/474,598.

Office action dated Mar. 8, 2018 for U.S. Appl. No. 15/341,260.

Office action dated Mar. 14, 2018 for U.S. Appl. No. 14/877,329.

Office action dated Mar. 21, 2018 for U.S. Appl. No. 14/879,525.

Office action dated Apr. 18, 2017 for U.S. Appl. No. 14/460,697.

Office action dated Apr. 23, 2015 for U.S. Appl. No. 13/474,599.

Office action dated Jun. 11, 2015 for U.S. Appl. No. 13/799,131.

Office Action dated Jun. 26, 2017 for U.S. Appl. No. 14/446,791.

Office action dated Jul. 9, 2015 for U.S. Appl. No. 13/474,598.

Office action dated Jul. 19, 2017 for U.S. Appl. No. 14/814,935.

Office action dated Aug. 6, 2015 for U.S. Appl. No. 13/474,598.

Office action dated Aug. 7, 2017 for U.S. Appl. No. 14/834,151.

Office action dated Aug. 8, 2017 for U.S. Appl. No. 14/814,935.

Office action dated Aug. 8, 2017 for U.S. Appl. No. 14/876,760.

Office action dated Aug. 10, 2017 for U.S. Appl. No. 14/460,697.

Office action dated Aug. 14, 2015 for U.S. Appl. No. 13/474,599.

Office action dated Aug. 22, 2017 for U.S. Appl. No. 15/341,260.

Office action dated Aug. 26, 2016 for U.S. Appl. No. 14/460,697.

Office action dated Aug. 27, 2015 for U.S. Appl. No. 13/474,598.

(56) References Cited

OTHER PUBLICATIONS

Office action dated Sep. 17, 2015 for U.S. Appl. No. 13/799,131.
Office action dated Oct. 19, 2016 for U.S. Appl. No. 14/446,791.
Office action dated Nov. 7, 2017 for U.S. Appl. No. 14/834,151.
Office action dated Nov. 16, 2017 for U.S. Appl. No. 14/814,935.
Office action dated Nov. 16, 2017 for U.S. Appl. No. 15/341,260.
Office action dated Nov. 27, 2017 for U.S. Appl. No. 14/876,760.
Office action dated Dec. 12, 2017 for U.S. Appl. No. 14/460,697.
"Office action dated Dec. 19, 2016 for U.S. Appl. No. 14/460,697".
Office action dated Dec. 21, 2017 for U.S. Appl. No. 14/919,281.
Powell, et al. Chemical speciation of environmentally significant metals with inorganic ligands. Pure Appl. Chem. 2007; 79(5):895-950.
Ralph, et al. Mass transport in an electrochemical laboratory filterpress reactor and its enhancement by turbulence promoters. Electrochemica Acta. 1996; 41(4):591-603.
Rollin, et al. The electrochemistry of nickel complexes with triphenylphosphine and ethylene in methylpyrrolidinone. Journal of Electroanalytical Chemistry and Interfacial Electrochemistry. 1985; 183(1-2):247-260.
Rorabacher. Electron transfer by copper centers. Chemical Centers. 2004; 104(2):651-698.
Spector, M.L. et al. 1967. Olefin Chlorination in Homogeneous Aqueous Copper Chloride Solutions. Industrial & Engineering Chemistry Process Design and Development. 6(3): 327-331.
Stanley, et al. Novel Organic Chemical Processes. Proceedings of the Royal Society of London. Series A, Mathematical and Physical Sciences 303.1474 (1968): 259-273.
U.S. Appl. No. 61/442,573, filed Feb. 14, 2011.
Wikipedia definition of "Aqueous Solution". Accessed Jul. 29, 2015. 2 pages.
Wikipedia definition of "Solvent". Accessed Jul. 29, 2015. 14 pages.
Nijhuis, et al. The Production of Propene Oxide: Catalytic Processes and Recent Developments. Industrial & Engineering Chemistry Research 2006 45 (10), 3447-3459 . . . .
PCT/US2018/029530 International Search Report and Written Opinion dated Jul. 11, 2018.
Richey. Chlorohydrins. Kirk-Ohmer Encyclopedia of Chemical Technology. 2000 . . . .
Trent, D.L., Propylene Oxide. In Kirk-Othmer:Encyclopedia of chemical technology; Wiley: New York, 2001. (Online electronic edition).
U.S. Appl. No. 15/338,235 Office Action dated Jun. 15, 2018.
EP16860934.5 Extended European Search Report dated May 9, 2019.
PCT/US2018/035010 International Search Report and Written Opinion dated Jul. 27, 2018.
U.S. Appl. No. 15/338,235 Notice of Allowance dated Jan. 24, 2019.
U.S. Appl. No. 16/424,878 Notice of Allowance dated Jan. 16, 2020.

\* cited by examiner

ELECTROCHEMICAL, CHLORINATION, AND OXYCHLORINATION SYSTEMS AND METHODS TO FORM PROPYLENE OXIDE OR ETHYLENE OXIDE

CROSS-REFERENCE TO RELATED APPLICATIONS

This application is a continuation-in-part of U.S. patent application Ser. No. 15/338,235, filed Oct. 28, 2016, and claims benefit of U.S. Provisional Application No. 62/490,903, filed Apr. 27, 2017; U.S. Provisional Application No. 62/528,273, filed Jul. 3, 2017; and U.S. Provisional Application No. 62/595,389, filed Dec. 6, 2017, all of which are incorporated herein by reference in their entirety in the present disclosure.

BACKGROUND

Polyurethane production remains one of the most environmentally challenging manufacturing processes in industrial polymerization. Formed from addition reactions of di-isocyanates and polyols, polyurethanes may have a significant embedded environmental footprint because of the challenges associated with both feedstocks. Polyols are themselves polymerization derivatives which use propylene oxide as raw materials. Traditionally, propylene oxide (PO) may be synthesized from a chlorinated intermediate, propylene chlorohydrin.

Ethylene oxide may be one of the important raw materials used in large-scale chemical production. Most ethylene oxide may be used for synthesis of ethylene glycols, including diethylene glycol and triethylene glycol, that may account for up to 75% of global consumption. Other important products may include ethylene glycol ethers, ethanolamines and ethoxylates. Among glycols, ethylene glycol may be used as antifreeze, in the production of polyester and polyethylene terephthalate (PET—raw material for plastic bottles), liquid coolants and solvents.

However, an environmentally acceptable process for the economic production of propylene oxide and ethylene oxide remains elusive. High costs of chlorine and significant waste water production (approximately 40 tons of waste water per tone of PO) has caused manufacturers to look for process options with reduced environmental and safety risks.

SUMMARY

There are provided methods and systems herein that relate to an environmentally friendly and low cost production of propylene oxide (PO) and ethylene oxide (EO).

In one aspect, there is provided a method comprising:
(i) contacting an anode with an anode electrolyte in an electrochemical cell wherein the anode electrolyte comprises metal chloride and saltwater; contacting a cathode with a cathode electrolyte in the electrochemical cell; applying voltage to the anode and the cathode and oxidizing the metal chloride with metal ion in a lower oxidation state to a higher oxidation state at the anode;
(ii) withdrawing the anode electrolyte from the electrochemical cell and chlorinating propylene with the anode electrolyte comprising the metal chloride with the metal ion in the higher oxidation state in the saltwater to result in one or more products comprising propylene chlorohydrin (PCH) and the metal chloride with the metal ion in the lower oxidation state; or withdrawing the anode electrolyte from the electrochemical cell and chlorinating ethylene with the anode electrolyte comprising the metal chloride with the metal ion in the higher oxidation state in the saltwater to result in one or more products comprising chloroethanol (CE) and the metal chloride with the metal ion in the lower oxidation state; and
(iii) epoxidizing the PCH or the CE with a base to form propylene oxide (PO) or ethylene oxide (EO), respectively.

In some embodiments of the aforementioned aspect, the one or more products from propylene further comprise 1,2-dichloropropane (DCP) or the one or more products from ethylene further comprise 1,2-dichloroethane (DCE).

In some embodiments of the aforementioned aspect and embodiments, the chlorination results in more than 20% yield of PCH or more than 50% yield of PCH. In some embodiments of the aforementioned aspect and embodiment, the chlorination results in more than 20% yield of CE or more than 50% yield of CE.

In some embodiments of the aforementioned aspect and embodiments, the method further comprises forming sodium hydroxide in the cathode electrolyte and using the sodium hydroxide as the base to form the propylene oxide or the ethylene oxide.

In some embodiments of the aforementioned aspect and embodiments, the one or more products from chlorinating propylene or ethylene further comprise hydrochloric acid (HCl). In some embodiments of the aforementioned aspect and embodiments, the method further comprises forming sodium hydroxide in the cathode electrolyte and using the sodium hydroxide to neutralize the HCl. In some embodiments of the aforementioned aspect and embodiments, the method further comprises oxychlorinating the metal chloride with the metal ion in the lower oxidation state after step (ii) to the higher oxidation state in presence of HCl and oxygen. In some embodiments, the HCl is from the chlorination reaction of the propylene or ethylene. In some embodiments of the aforementioned aspect and embodiments, the methods further comprise separating the PCH or the CE and other organic products from the HCl and the metal chloride with the metal ion in the lower oxidation state after step (ii) and subjecting the HCl and the metal chloride with the metal ion in the lower oxidation state to the oxychlorination step.

In some embodiments of the aforementioned aspect and embodiments, the method further comprises recirculating the metal chloride in the higher oxidation state back to step (ii).

In one aspect, there are provided methods, comprising:
(i) oxychlorinating a metal chloride with the metal ion in a lower oxidation state to a higher oxidation state in presence of HCl and oxygen;
(ii) withdrawing the metal chloride with the metal ion in the higher oxidation state and chlorinating propylene with the metal chloride with the metal ion in the higher oxidation state to result in one or more products comprising propylene chlorohydrin (PCH) and the metal chloride with the metal ion in the lower oxidation state; or withdrawing the metal chloride with the metal ion in the higher oxidation state and chlorinating ethylene with the metal chloride with the metal ion in the higher oxidation state to result in one or more products comprising chloroethanol (CE) and the metal chloride with the metal ion in the lower oxidation state; and
(iii) epoxidizing the PCH or the CE with a base to form propylene oxide (PO) or ethylene oxide (EO), respectively.

In some embodiments of the aforementioned aspect, the one or more products from propylene further comprise DCP or the one or more products from ethylene further comprise 1,2-dichloroethane (DCE). In some embodiments of the aforementioned aspect and embodiments, the method further comprises hydrolyzing the DCP to the PCH or hydrolyzing the DCE to the CE.

In some embodiments of the aforementioned aspects and embodiments, the oxidizing, the chlorinating and the oxychlorinating steps are carried out in saltwater.

In some embodiments of the aforementioned aspects and embodiments, the saltwater comprises alkali metal chloride. In some embodiments of the aforementioned aspects and embodiments, the alkali metal chloride is sodium chloride, lithium chloride, or potassium chloride.

In some embodiments of the aforementioned aspects and embodiments, the methods further comprise separating the one or more products from the metal chloride in the saltwater.

In some embodiments of the aforementioned aspects and embodiments, the methods further comprise separating the PCH or CE from the metal chloride in the saltwater.

In some embodiments of the aforementioned aspects and embodiments, the concentration of the metal chloride with the metal ion in the lower oxidation state entering the oxychlorination reaction is between about 0.5-2M; concentration of the metal chloride with the metal ion in the lower oxidation state entering the chlorination reaction is between about 0.1-1.8M; concentration of the metal chloride with the metal ion in the lower oxidation state entering the electrochemical reaction is between about 0.6-2.5M; or combinations thereof.

In some embodiments of the aforementioned aspects and embodiments, the methods further comprise separating the metal chloride solution from the one or more products comprising PCH or the CE after the chlorinating step and delivering the metal chloride solution back to the electrochemical reaction and/or the oxychlorination reaction.

In some embodiments of the aforementioned aspects and embodiments, the yield of the PO or EO is more than 90 wt % and/or the space time yield (STY) of the PO or EO is more than 0.1.

In some embodiments of the aforementioned aspects and embodiments, the metal chloride with the metal ion in the lower oxidation state is CuCl and the metal chloride with the metal ion in the higher oxidation state is $CuCl_2$.

In one aspect, there are provided methods, comprising:

(i) contacting chlorine gas with a solution comprising metal chloride and oxidizing the metal chloride with metal ion in a lower oxidation state to a higher oxidation state with the chlorine gas;

(ii) chlorinating propylene with the metal chloride with the metal ion in the higher oxidation state in the solution to result in one or more products comprising propylene chlorohydrin (PCH) and the metal chloride with the metal ion in the lower oxidation state; or chlorinating ethylene with the metal chloride with the metal ion in the higher oxidation state in the solution to result in one or more products comprising chloroethanol (CE) and the metal chloride with the metal ion in the lower oxidation state; and (iii) epoxidizing the PCH or the CE with a base to form propylene oxide (PO) or ethylene oxide (EO), respectively.

In some embodiments of the aforementioned aspect and embodiments, the methods further comprise obtaining the chlorine gas from an electrochemical process wherein the process comprises contacting an anode with an anode electrolyte wherein the anode electrolyte comprises saltwater; contacting a cathode with a cathode electrolyte; applying a voltage to the anode and the cathode and oxidizing the salt water to hydroxide ions at the cathode and chlorine gas at the anode.

In some embodiments of the aforementioned aspect and embodiments, the one or more products from propylene further comprise 1,2-dichloropropane (DCP) or the one or more products from ethylene further comprise 1,2-dichloroethane (DCE).

In some embodiments of the aforementioned aspect and embodiments, the methods further comprise forming sodium hydroxide in the cathode electrolyte and using the sodium hydroxide as the base to form the propylene oxide or the ethylene oxide.

In some embodiments of the aforementioned aspect and embodiments, the one or more products from propylene or ethylene further comprise hydrochloric acid (HCl). In some embodiments of the aforementioned aspect and embodiments, the method further comprise forming sodium hydroxide in the cathode electrolyte and using the sodium hydroxide to neutralize the HCl.

In some embodiments of the aforementioned aspect and embodiments, the methods further comprise oxychlorinating the metal chloride with the metal ion in the lower oxidation state after step (ii) to the higher oxidation state in presence of the HCl and oxygen.

In some embodiments of the aforementioned aspect and embodiments, the methods further comprise recirculating the metal chloride in the higher oxidation state back to step (i) and/or (ii).

In one aspect, there is provided a system, comprising:

an electrochemical cell comprising an anode in contact with an anode electrolyte wherein the anode electrolyte comprises metal chloride and saltwater; a cathode in contact with a cathode electrolyte; and a voltage source configured to apply a voltage to the anode and the cathode wherein the anode is configured to oxidize the metal chloride with the metal ion from a lower oxidation state to a higher oxidation state; and/or an oxychlorination reactor operably connected to the electrochemical cell and/or chlorination reactor and configured to oxychlorinate the metal chloride with the metal ion from the lower oxidation state to the higher oxidation state in presence of HCl and oxygen;

a chlorination reactor operably connected to the electrochemical cell and/or the oxychlorination reactor wherein the chlorination reactor is configured to receive the metal chloride with the metal ion in the higher oxidation state from the electrochemical cell and/or configured to receive the metal chloride solution with the metal ion in the higher oxidation state from the oxychlorination reactor and chlorinate propylene or ethylene with the metal chloride with the metal ion in the higher oxidation state to result in one or more products comprising PCH or one or more products comprising CE, respectively, and the metal chloride solution with the metal ion in the lower oxidation state; and an epoxide reactor operably connected to the chlorination reactor and configured to epoxidize PCH or CE with a base to form PO or EO, respectively.

In some embodiments of the aforementioned aspect, the electrochemical cell, the chlorination reactor and the oxychlorination reactor are all configured to carry out the reactions in saltwater.

BRIEF DESCRIPTION OF THE DRAWINGS

The novel features of the invention are set forth with particularity in the appended claims. A better understanding of the features and advantages of the present invention may be obtained by reference to the following detailed description that sets forth illustrative embodiments, in which the principles of the invention are utilized, and the accompanying drawings of which:

DETAILED DESCRIPTION

Figure 1A:
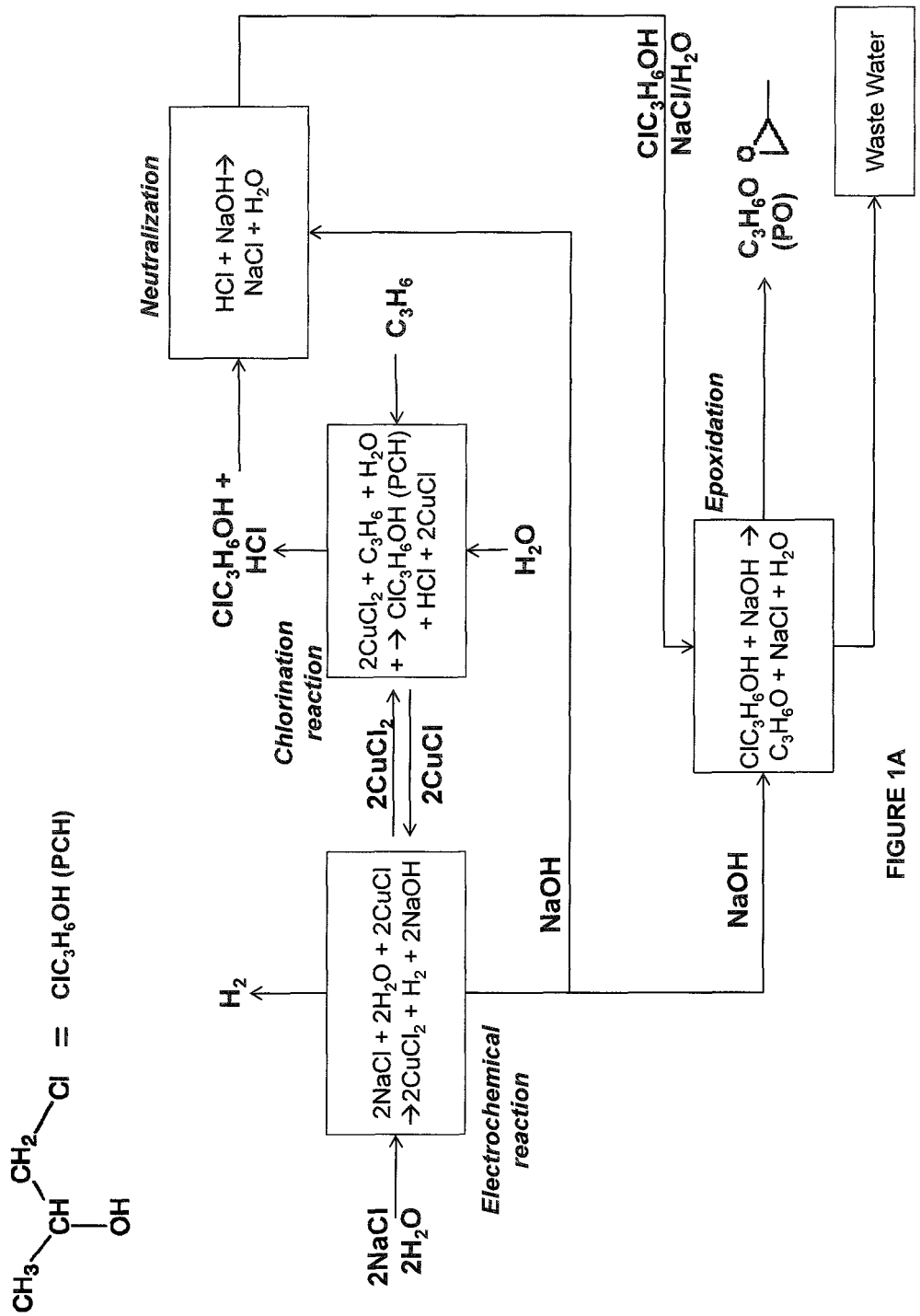
FIG. 1A is an illustration of some embodiments related to the electrochemical reaction, the chlorination reaction, and the epoxidation reaction using propylene.

Disclosed herein are systems and methods that relate to various combinations of an electrochemical system, chlorination system, oxychlorination system, and epoxidation system, to form propylene oxide (PO) or ethylene oxide (EO). These combined systems provide an efficient, low cost, and low energy consuming systems that use metal chloride redox shuttles to form propylene chlorohydrin (exclusively or with formation of 1,2-dichloropropane (DCP)) from propylene and its subsequent epoxidation to PO; or to form chloroethanol (exclusively or with formation of 1,2-dichloroethane (DCE)) from ethylene and its subsequent epoxidation to EO.

The "propylene chlorohydrin" or "PCH" as used herein is also known as chloropropyl alcohol and may be present in one or more of its isomeric forms such as, 1-hydroxy-2-chloropropane, 1-chloro-2-hydroxy propane, or combination thereof. The "chloroethanol" or "CE" as used herein is also known as 2-chloro ethanol, ethylchlorhydrin, or ethylene chlorohydrin (ECH), etc. The "1,2-dichloroethane" or "DCE" as used herein is also known as ethylene dichloride or EDC. The "1,2-dichloropropane" or "DCP" as used herein is also known as propylene dichloride or PDC.

As can be appreciated by one ordinarily skilled in the art, the present electrochemical system and method can be configured with an alternative, equivalent salt solution, e.g., an alkali metal ion or alkaline earth metal ion solution, e.g. potassium chloride solution or sodium chloride solution or lithium chloride solution or a magnesium chloride solution or calcium chloride solution or sodium sulfate solution or ammonium chloride solution, to optionally produce an equivalent alkaline solution, e.g., potassium hydroxide or sodium hydroxide or magnesium hydroxide in the cathode electrolyte (or other reactions at the cathode described herein). This salt solution can be used as an anode electrolyte, cathode electrolyte, and/or brine in the middle compartment. Accordingly, to the extent that such equivalents are based on or suggested by the present system and method, these equivalents are within the scope of the application.

Before the present invention is described in greater detail, it is to be understood that this invention is not limited to particular embodiments described, as such may, of course, vary. It is also to be understood that the terminology used herein is for the purpose of describing particular embodiments only and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges that are presented herein with numerical values may be construed as "about" numerical. The "about" is to provide literal support for the exact number that it precedes, as well as a number that is near to or approximately the number that the term precedes. In determining whether a number is near to or approximately a specifically recited number, the near or approximating unrequited number may be a number, which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a," "an," and "the" include plural references unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods and Systems

There are provided methods and systems that relate to various combinations of an electrochemical system, chlorination system, oxychlorination system and epoxidation system, to form propylene oxide (PO) or ethylene oxide (EO). The electrochemical and chlorination methods and systems have been described in detail in U.S. patent application Ser. No. 13/474,598, filed May 17, 2012, issued as U.S. Pat. No. 9,187,834, on Nov. 17, 2015, which is incorporated herein by reference in its entirety.

Applicants surprisingly found that the combination of systems as described herein enhances the yield and selectivity of PCH and PO or CE and EO and/or reduces the voltage of the electrochemical cell. In some embodiments, the integration of the systems also results in reuse of the side products. For example, in some embodiments, the integration of the oxychlorination system may also result in the use of HCl as an oxidant which is a side product formed during chlorination reaction of propylene to form PCH or ethylene to form CE. Similarly, in some embodiments, the sodium hydroxide formed at the cathode in the electrochemical cell may be used to neutralize the HCl formed during other reactions and/or used to epoxidize PCH to PO or CE to EO. Many such variations have been described herein.

In one aspect, there are provided methods that include (i) contacting an anode with an anode electrolyte in an electrochemical cell wherein the anode electrolyte comprises metal chloride and saltwater; contacting a cathode with a cathode electrolyte in the electrochemical cell; applying a voltage to the anode and the cathode and oxidizing the metal chloride with metal ion in a lower oxidation state to a higher oxidation state at the anode;

(ii) withdrawing the anode electrolyte from the electrochemical cell and chlorinating propylene with the anode electrolyte comprising the metal chloride with the metal ion in the higher oxidation state in the saltwater to result in one or more products comprising propylene chlorohydrin (PCH) and the metal chloride with the metal ion in the lower oxidation state; or withdrawing the anode electrolyte from the electrochemical cell and chlorinating ethylene with the anode electrolyte comprising the metal chloride with the metal ion in the higher oxidation state in the saltwater to result in one or more products comprising chloroethanol (CE) and the metal chloride with the metal ion in the lower oxidation state; and (iii) epoxidizing the PCH or the CE with a base to form propylene oxide (PO) or ethylene oxide (EO), respectively.

It is to be understood that one or more combinations of these steps may be carried out together. For example, the step (iii) in series with the step (ii) and the step (i) in series or in parallel with the step (ii) and/or (iii). The steps may be integrated in a single unit or may be more than one separate units running in a plant. Similarly, other combinations may be carried out in a single unit or as separate units in one plant.

In some embodiments, there are provided systems that carry out the methods described herein.

In some embodiments, there are provided systems that include an electrochemical cell comprising an anode in contact with an anode electrolyte wherein the anode electrolyte comprises metal chloride and saltwater; a cathode in contact with a cathode electrolyte; and a voltage source configured to apply a voltage to the anode and the cathode wherein the anode is configured to oxidize the metal chloride with the metal ion from a lower oxidation state to a higher oxidation state;

a chlorination reactor operably connected to the electrochemical cell wherein the chlorination reactor is configured to receive the metal chloride with the metal ion in the higher oxidation state from the electrochemical cell and chlorinate propylene or ethylene with the metal chloride with the metal ion in the higher oxidation state to result in one or more products comprising PCH or one or more products comprising CE, respectively, and the metal chloride solution with the metal ion in the lower oxidation state; and an epoxide reactor operably connected to the chlorination reactor and configured to epoxidize PCH or CE with a base to form PO or EO, respectively.

In some embodiments of the above noted system, the system further comprises means for transferring NaOH formed in the cathode chamber of the electrochemical cell to the neutralizing chamber for neutralizing HCl formed in the chlorination reactor and/or means for transferring NaOH formed in the cathode chamber of the electrochemical cell to the epoxidation reactor for the epoxidation of PCH to PO or CE to EO. Such means include any means for transferring liquids including, but not limited to, conduits, tanks, pipes, and the like.

Figure 1B:
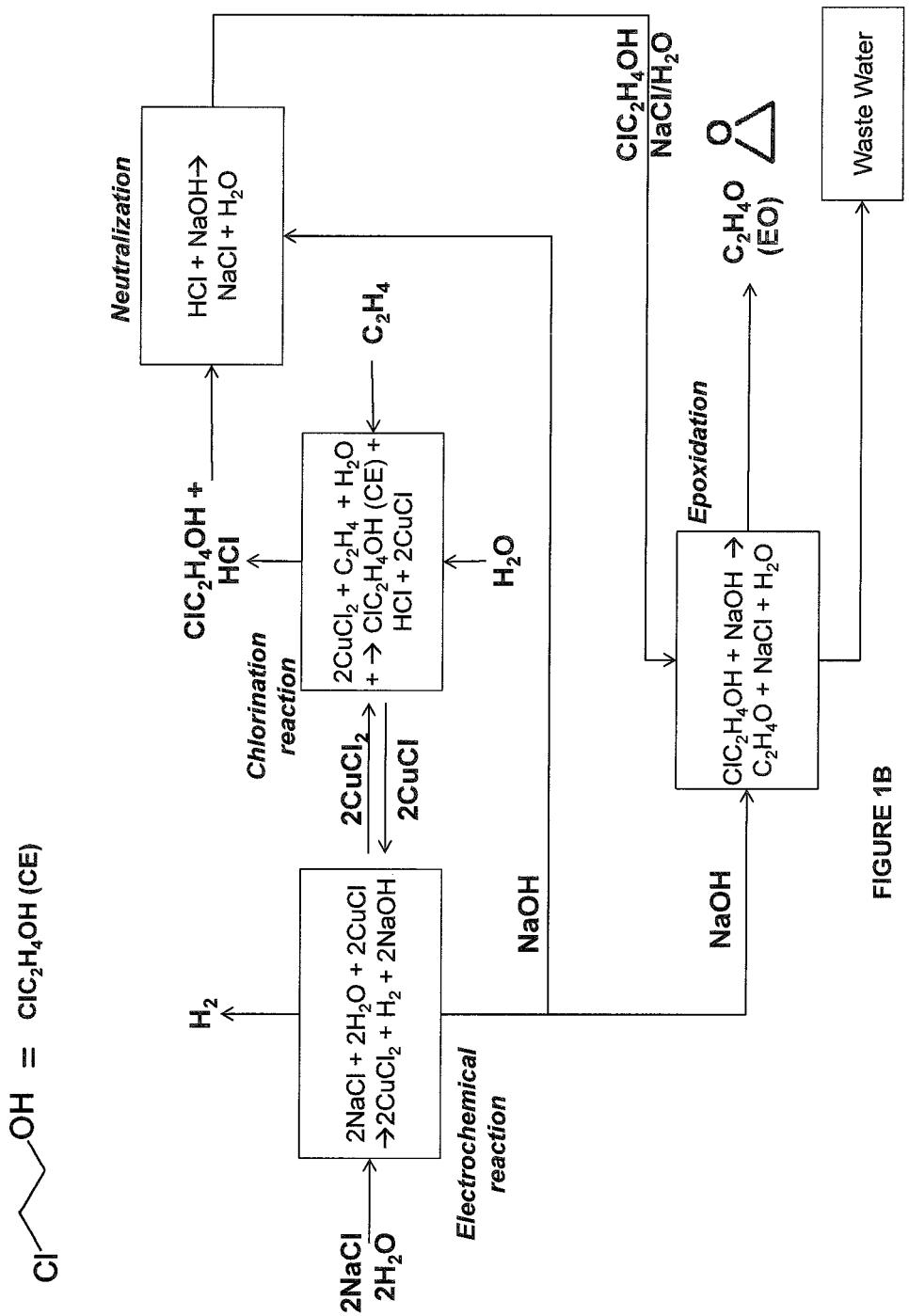
FIG. 1B is an illustration of some embodiments related to the electrochemical reaction, the chlorination reaction, and the epoxidation reaction using ethylene.

Above noted aspect is as illustrated in FIGS. 1A and 1B. In the electrochemical reaction, a metal chloride, e.g. CuCl is oxidized at the anode to higher oxidation state $CuCl_2$ in saltwater (illustrated as sodium chloride (NaCl)) when sodium hydroxide (NaOH) and hydrogen gas are formed at the cathode). It is to be understood that the metal chloride illustrated as CuCl and $CuCl_2$, saltwater illustrated as NaCl, and the cathode reaction to form NaOH and $H_2$ gas, in all the figures herein, are for illustration purposes only and other variations of the metal chloride and other cathode reactions are well within the scope of the invention and have been described in detail herein. The anode electrolyte comprising NaCl and $CuCl_2$ is withdrawn from the electrochemical cell and is subjected to chlorination of propylene in the chlorination reaction when propylene ($C_3H_6$) is chlorinated to propylene chlorohydrin (PCH) (or chlorination of ethylene ($C_2H_4$) to chloroethanol (CE)) and $CuCl_2$ is reduced to CuCl (metal ion from the higher oxidation state to the lower oxidation state). In the figures illustrated herein, the PCH is illustrated as 1-chloro-2-hydroxy form, however, 2-chloro-1-hydroxy form may also be formed in combination or in isolation. During the chlorination reaction, hydrochloric acid is formed (HCl) which is neutralized with NaOH formed at the cathode. Another mole of NaOH from the cathode electrolyte may be used to epoxidize PCH to propylene oxide (PO) or to epoxidize CE to ethylene oxide (EO) in the epoxidation reaction. After the chlorination reaction, the one or more products comprising PCH from propylene or one or more products comprising CE from ethylene may be separated from the aqueous medium (water containing metal chloride and salts and optionally HCl) using various separation techniques described further herein below. The separated one or more products may or may not be subjected to purification before the PCH is epoxidized to PO or before CE is epoxidized to EO. The water comprising metal chlorides and salts may be recirculated back to the electrochemical cell for further oxidation of the metal ions at the anode.

The "chlorination" or its grammatical equivalent, as used herein, includes a reaction of propylene or ethylene with the metal chloride with the metal ion in the higher oxidation state to form one or more products. The "one or more products" used herein includes organic and inorganic products formed during the chlorination reaction. The organic one or more products comprise PCH (including enantiomers thereof) and other side products formed during the reaction with propylene or the organic one or more products comprise CE and other side products formed during the reaction with ethylene. In some embodiments of the above noted aspect, the one or more products from propylene further comprise 1,2-dichloropropane (DCP) or the one or more products from ethylene further comprise 1,2-dichloroethane (DCE). In some embodiments of the above noted aspect and embodiments, the chlorination results in more than 10%; or more than 20%; or more than 30%; or more than 40%; or more than 50%; or more than 60%; or more than 70%; or more than 80%; or more than 90% yield of PCH or CE. In some embodiments, the remaining % is of DCP and/or other side products from propylene or the remaining % is of DCE and/or other side products from ethylene.

The side products include, without limitation, 1,2-dichloropropane (including enantiomers thereof) and other chlorinated derivatives from propylene and 1,2-dichloroethane and other chlorinated derivatives from ethylene. PCH or CE may be separated from other side products using separation techniques described herein. Example of inorganic products includes, without limitation, HCl. The HCl may be formed in the chlorination reaction and may be present in the saltwater along with metal chlorides. In some embodiments, the PCH or CE and other organic side products may be separated from the aqueous medium (saltwater containing metal chlorides and HCl) and the HCl solution may be neutralized with NaOH.

In the chlorination reactor, the propylene or ethylene may be supplied under pressure in the gas phase and the metal chloride, for example only, copper(II) chloride (also containing copper(I) chloride) is supplied in an aqueous solution originating from the outlet of the anode chamber of the electrochemical cell and/or originating from the outlet of the oxychlorination reactor. The reaction may occur in the liquid phase where the dissolved propylene or ethylene reacts with the copper(II) chloride. The reaction may be carried out at pressures between 270 psig and 530 psig to improve propylene or ethylene solubility in the aqueous phase. After the reaction, the metal ion in the higher oxidation state is reduced to metal ion in the lower oxidation state. The metal ion solution is separated from the one or more products (organics) in a separator before the metal ion solution is recirculated back to the anode electrolyte of the electrochemical system or to the solution in the oxychlorination reactor. It is to be understood that the metal chloride solution going into the anode electrolyte and the metal chloride solution coming out of the anode electrolyte contains a mix of the metal chloride in the lower oxidation state and the higher oxidation state except that the metal chloride solution coming out of the anode chamber has higher amount of metal chloride in the higher oxidation state than the metal chloride solution going into the anode electrolyte.

In some embodiments of the foregoing embodiments, the one or more reaction conditions for the chlorination mixture or reaction mixture in the chlorination reactor are selected from temperature of between about 120-250° C.; incubation time of between about 1 sec-3 hour; concentration of the metal chloride in the higher oxidation state at more than 4M or between 4.5-8M, and combinations thereof.

As illustrated in FIGS. 1A and 1B, two copper chlorides are converted in the electrochemical reaction for every propylene oxide or ethylene oxide that is produced. Since the propylene oxide or ethylene oxide does not contain any chloride, these chlorides are ultimately neutralized by 2NaOH molecules (also generated in the electrochemical reaction). In the above method, the OpEx savings compared to a chlor-alkali process (commercial process that electrochemically produces chlorine gas which is then used for chlorination reaction) may be derived from the lower operating voltage of the cell. For example only, compared to a chlor-alkali unit operating at 3V (to generate $Cl_2$ for chlorination), the electrochemical cell in FIGS. 1A and 1B may effectively be operating at about 2.2-2.6V.

In some embodiments of the above noted aspect and embodiments, the method further comprises forming sodium hydroxide in the cathode electrolyte and using the sodium hydroxide as the base to form the propylene oxide or ethylene oxide.

The "base" used herein in the epoxidation reaction may be any known base in the art. Examples include, without limitation, alkali metal hydroxides, alkaline earth metal hydroxides, and the like. In some embodiments, the sodium hydroxide in the cathode electrolyte is used as the base optionally supplemented with other bases as listed above.

In some embodiments of the above noted aspect and embodiments, the one or more products in the chlorination reaction further comprise hydrochloric acid (HCl). In some embodiments of the above noted aspect and embodiments, the method further comprises forming sodium hydroxide in the cathode electrolyte and using the sodium hydroxide to neutralize the HCl.

In some embodiments of the above noted aspect and embodiments, the method further comprises oxychlorinating the metal chloride with the metal ion in the lower oxidation state after step (ii) to the higher oxidation state in presence of the HCl and oxygen (or other oxidants listed herein).

Accordingly, there are provided methods that include (i) contacting an anode with an anode electrolyte in an electrochemical cell wherein the anode electrolyte comprises metal chloride and saltwater; contacting a cathode with a cathode electrolyte in the electrochemical cell; applying voltage to the anode and the cathode and oxidizing the metal chloride with metal ion in a lower oxidation state to a higher oxidation state at the anode;

(ii) withdrawing the anode electrolyte from the electrochemical cell and chlorinating propylene with the anode electrolyte comprising the metal chloride with the metal ion in the higher oxidation state in the saltwater to result in one or more products comprising propylene chlorohydrin (PCH) and the metal chloride with the metal ion in the lower oxidation state; or withdrawing the anode electrolyte from the electrochemical cell and chlorinating ethylene with the anode electrolyte comprising the metal chloride with the metal ion in the higher oxidation state in the saltwater to result in one or more products comprising chloroethanol (CE) and the metal chloride with the metal ion in the lower oxidation state;

(iii) oxychlorinating the metal chloride with the metal ion in the lower oxidation state after step (ii) to the higher oxidation state in presence of the HCl and oxygen; and (iv) epoxidizing the PCH or the CE with a base to form propylene oxide (PO) or ethylene oxide (EO), respectively.

The "oxychlorination" or its grammatical equivalent, as used herein, includes a reaction in which an oxidant oxidizes a metal ion of a metal chloride from a lower oxidation state to a higher oxidation state. The oxidant includes one or more oxidizing agents that oxidize the metal ion of the metal chloride from the lower to the higher oxidation state. Examples of oxidants include, without limitation, HCl gas and/or HCl solution in combination with gas comprising oxygen or ozone. Other oxidants that may be used to supplement the foregoing oxidants include, without limitation, hydrogen peroxide, HClO or salt thereof, $HClO_3$ or salt thereof, $HClO_4$ or salt thereof, or combinations thereof.

The gas comprising oxygen can be any gas comprising more than 1% oxygen; or more than 5% oxygen; or more than 10% oxygen; or more than 20% oxygen; or more than 30% oxygen; or more than 40% oxygen; or more than 50% oxygen; or between 1-30% oxygen; or between 1-25% oxygen; or between 1-20% oxygen; or between 1-15% oxygen; or between 1-10% oxygen; or is atmospheric air (about 21% oxygen). In some embodiments, when oxygen depolarizing cathode (ODC) is used in the cathode chamber of the electrochemical cell (described in detail below), then the oxygen introduced in the cathode chamber may also be used for the oxychlorination reaction. In some embodiments, the oxygen that exits the cathode chamber after being used at the ODC, may be collected and transferred to the oxychlorination reactor for the oxychlorination reaction. In some embodiments, the cathode chamber may be operably connected to the oxychlorination reactor for the circulation of the oxygen gas.

In some embodiments, when the oxidant is HCl gas and/or HCl solution in combination with air, the air deprived of the oxygen (after reaction in the oxychlorination reactor) and rich in nitrogen may be collected, optionally compressed, and sold in the market.

In some embodiments, the gas may comprise ozone alone or in combination with oxygen gas. In some embodiments, the gas comprising ozone can be any gas comprising more than 0.1% ozone; or more than 1% ozone; or more than 10% ozone; or more than 20% ozone; or more than 30% ozone; or more than 40% ozone; or more than 50% ozone; or between 0.1-30% ozone; or between 0.1-25% ozone; or between 0.1-20% ozone; or between 0.1-15% ozone; or between 0.1-10% ozone.

In some embodiments, the concentration of the oxidant solution (e.g. HCl) is between about 0.1-10M; or 0.1-5M; or 0.1-1M; or 5-10M; or 1-5M.

In some embodiments, the ratio of the HCl gas and/or HCl solution (I) and the gas comprising oxygen or ozone (II), i.e. I:II is 1:1 or 2:1 or 3:1 or 2:0.5 or 2:0.1 or 1:0.1 or 1:0.5.

In some embodiments, the HCl gas or HCl solution used as an oxidant is obtained from the vinyl chloride monomer (VCM) process. In some embodiments, when the ethylene is reacted with the metal chloride with the metal ion in the higher oxidation state to form ethylene dichloride (chlorination reaction). The EDC thus formed, may be used in the cracking process to form VCM which may also produce HCl. The HCl may be separated from the VCM using techniques, such as, but not limited to, distillation to separate VCM from HCl. The HCl may then be used in the oxychlorination process of the invention.

In some embodiments, the HCl gas or HCl solution used as an oxidant is obtained from the chlorination process. For example, when propylene is chlorinated with $CuCl_2$ to form PCH, the chlorination may result in the formation of HCl. The HCl thus formed may optionally be separated from the organics and may be used in the oxychlorination reaction.

In some embodiments, there are provided systems that carry out the above noted method described herein.

In some embodiments, there are provided systems that include an electrochemical cell comprising an anode in contact with an anode electrolyte wherein the anode electrolyte comprises metal chloride and saltwater; a cathode in contact with a cathode electrolyte; and a voltage source configured to apply voltage to the anode and the cathode wherein the anode is configured to oxidize the metal chloride with the metal ion from a lower oxidation state to a higher oxidation state;

a chlorination reactor operably connected to the electrochemical cell wherein the chlorination reactor is configured to receive the metal chloride with the metal ion in the higher oxidation state from the electrochemical cell and chlorinate propylene or ethylene with the metal chloride with the metal ion in the higher oxidation state to result in one or more products comprising PCH or one or more products comprising CE, respectively, and the metal chloride solution with the metal ion in the lower oxidation state;

an oxychlorination reactor operably connected to the chlorination reactor and configured to oxychlorinate the metal chloride with the metal ion from the lower oxidation state to the higher oxidation state in presence of HCl and oxygen; and an epoxide reactor operably connected to the chlorination reactor and/or the oxychlorination reactor and configured to epoxidize the PCH or CE with a base to form PO or EO, respectively.

In some embodiments, when the oxidant is HCl gas and/or HCl solution in combination with gas comprising oxygen or ozone, the HCl gas and/or HCl solution as well as the gas comprising oxygen or ozone may be administered to the oxychlorination reactor. The reactor may also receive the aqueous solution of metal chloride with the metal ion in the lower oxidation state. The solution may be the anode electrolyte comprising saltwater and the metal chloride or the solution may be the saltwater from the chlorination reactor. The oxychlorination reactor may be any column, tube, tank, pipe, or reactors that can carry out the oxychlorination reaction. The reactor may be fitted with various probes including temperature probe, pH probe, pressure probe, etc. to monitor the reaction. The reaction may be heated with means to heat the reaction mixture. The temperature of the reactor may be between about 40-160° C. or between about 100-150° C. and/or the pressure in the oxychlorination reactor may be between about 100-300 psig or between about 150-250 psig or between about 150-300 psig. The oxychlorination reaction may be carried out for between about 5 min-120 min to few hours. The oxychlorination reactor may also be fitted with conduits for the entry and/or exit of the solutions and the gases. Other detailed descriptions of the reactor are provided herein.

In some embodiments of the above noted system, the system further comprises means for transferring HCl and metal chloride in the lower oxidation state, formed in the chlorination reactor to the oxychlorination reactor and/or means for transferring metal chloride in the higher oxidation state from the oxychlorination reactor to the chlorination reactor. Such means include any means for transferring liquids including, but not limited to, conduits, tanks, pipes, and the like.

Figure 2A:
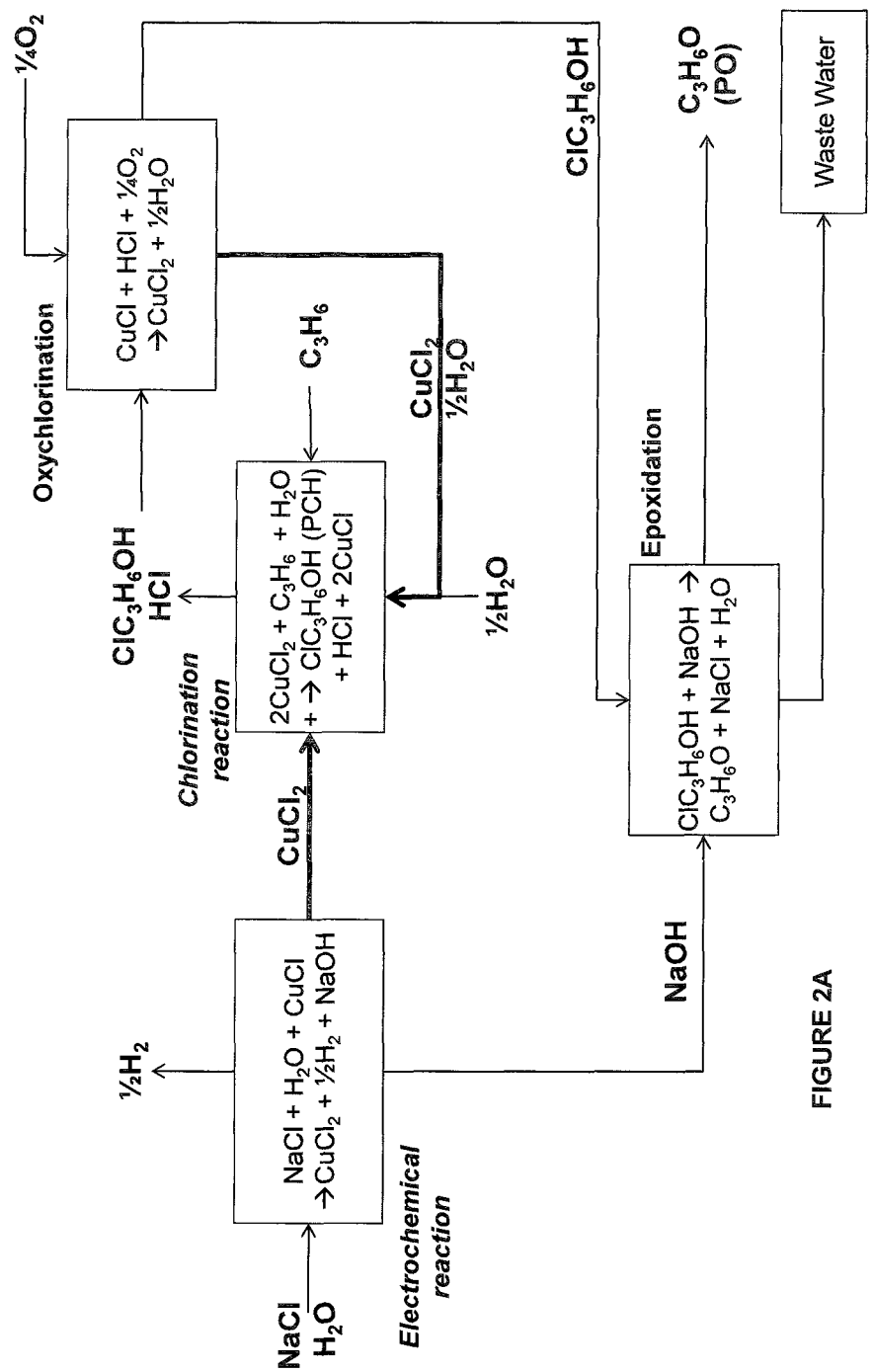
FIG. 2A is an illustration of some embodiments related to the electrochemical reaction, the chlorination reaction, the oxychlorination reaction, and the epoxidation reaction using propylene.
Figure 2B:
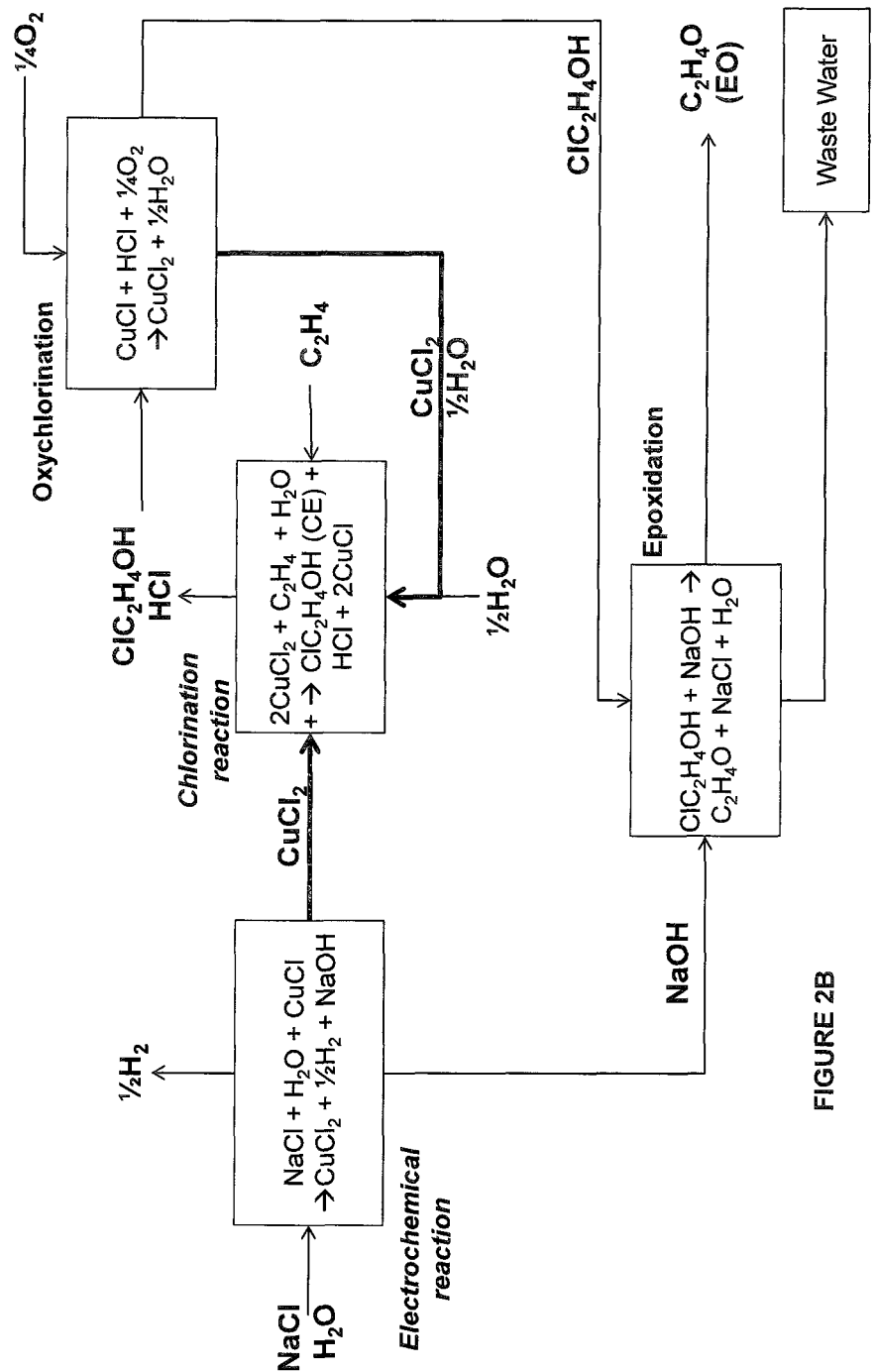
FIG. 2B is an illustration of some embodiments related to the electrochemical reaction, the chlorination reaction, the oxychlorination reaction, and the epoxidation reaction using ethylene.

This embodiment is illustrated in FIGS. 2A and 2B, where the CuCl and HCl generated in the chlorination reaction are subjected to oxychlorination reaction in the presence of oxygen (or any other oxidizing gas) to oxidize CuCl back to $CuCl_2$. The $CuCl_2$ can then be recirculated back to the chlorination reaction for chlorination of propylene or ethylene. As illustrated in FIGS. 2A and 2B, CuCl is oxidized to $CuCl_2$ in the anode chamber of the electrochemical cell. The saltwater from the anode chamber of the electrochemical cell containing the $CuCl_2$ is transferred to the chlorination reaction where a reaction with propylene ($C_3H_6$) or reaction with ethylene ($C_2H_4$) produces one or more products comprising PCH or CE, respectively, and $CuCl_2$ is reduced to CuCl. The aqueous solution from the chlorination reaction containing the CuCl (also containing $CuCl_2$) is separated from the PCH or the CE and is transferred to the oxychlorination reaction where the HCl and oxygen (or any other oxidizing gas such as ozone) oxidizes the CuCl to $CuCl_2$. The $CuCl_2$ solution (also containing CuCl) is then transferred from the oxychlorination reaction back to the chlorination reaction.

The method illustrated in FIGS. 2A and 2B uses the HCl generated in the chlorination reaction as a source of a chloride ion for an oxychlorination step. The oxychlorination step now regenerates half of the $CuCl_2$ for the chlorination reaction, while the electrochemical cell regenerates the other half of $CuCl_2$. As a result, the electrochemical cell's power demand is cut in half when compared to the method illustrated in FIGS. 1A and 1B. For example only, compared to a chlor-alkali unit operating at about 3V (to generate $Cl_2$ for chlorination), the electrochemical cell in FIGS. 2A and 2B may effectively be operating at about 2.4V or between about 2.2-2.6V, but half as many cells would be needed. In addition, there may be savings in salt demand and cell CapEx.

In some embodiments, the above noted system further comprises a conduit or a pipe or a delivery system (fitted with valves etc.) operably connected between the chlorination reactor and the oxychlorination reactor configured for delivering the metal chloride with the metal ion in the lower oxidation state in the saltwater of the chlorination reactor to the oxychlorination reactor wherein the oxychlorination reactor oxychlorinates the metal chloride with the metal ion from the lower oxidation state to the higher oxidation state. In some embodiments, the system further comprises a conduit or a pipe or a delivery system (fitted with valves etc.) operably connected between the oxychlorination reactor and the chlorination reactor configured for delivering the metal chloride with the metal ion in the higher oxidation state in the saltwater of the oxychlorination reactor to the chlorination reactor. In some embodiments, the system further comprises a separator (not shown in the figures) operably connected to the chlorination reactor and the oxychlorination reactor configured to receive the solution of the one or more products and the metal chloride with the metal ion in the lower oxidation state from the chlorination reactor, and to separate the one or more products from the metal chloride in the saltwater after the chlorination reactor. In some embodiments, the separator is further configured to deliver the metal chloride with the metal ion in the lower oxidation state to the oxychlorination reactor and the one or more products comprising PCH or CE to the epoxidation reactor. The aqueous solution (or the saltwater) containing the metal chloride with the metal ion in the lower oxidation state separated from the one or more products further includes HCl for oxychlorination. Various separation and purification methods and systems have been described in U.S. patent application Ser. No. 14/446,791, filed Jul. 30, 2014, which is incorporated herein by reference in its entirety in the present disclosure. Some examples of the separation techniques include without limitation, reactive distillation, adsorbents, liquid-liquid separation, liquid-vapor separation, etc.

The examples of conduits include, without limitation, pipes, tubes, tanks, and other means for transferring the liquid solutions. In some embodiments, the conduits attached to the systems also include means for transferring gases such as, but not limited to, pipes, tubes, tanks, and the like. The gases include, for example only, propylene gas or ethylene gas to the chlorination reactor, oxygen or ozone gas to the oxychlorination reactor, or the oxygen gas to the cathode chamber of the electrochemical cell etc.

In one aspect, there is provided a method that includes (i) oxychlorinating a metal chloride with the metal ion in a lower oxidation state to a higher oxidation state in presence of HCl and oxygen;

(ii) withdrawing the metal chloride with the metal ion in the higher oxidation state and chlorinating propylene with the metal chloride with the metal ion in the higher oxidation state to result in one or more products comprising propylene chlorohydrin (PCH) and the metal chloride with the metal ion in the lower oxidation state; or withdrawing the metal chloride with the metal ion in the higher oxidation state and chlorinating ethylene with the metal chloride with the metal ion in the higher oxidation state to result in one or more products comprising chloroethanol (CE) and the metal chloride with the metal ion in the lower oxidation state; and (iii) epoxidizing the PCH or the CE with a base to form propylene oxide (PO) or ethylene oxide (EO), respectively.

Figure 3A:
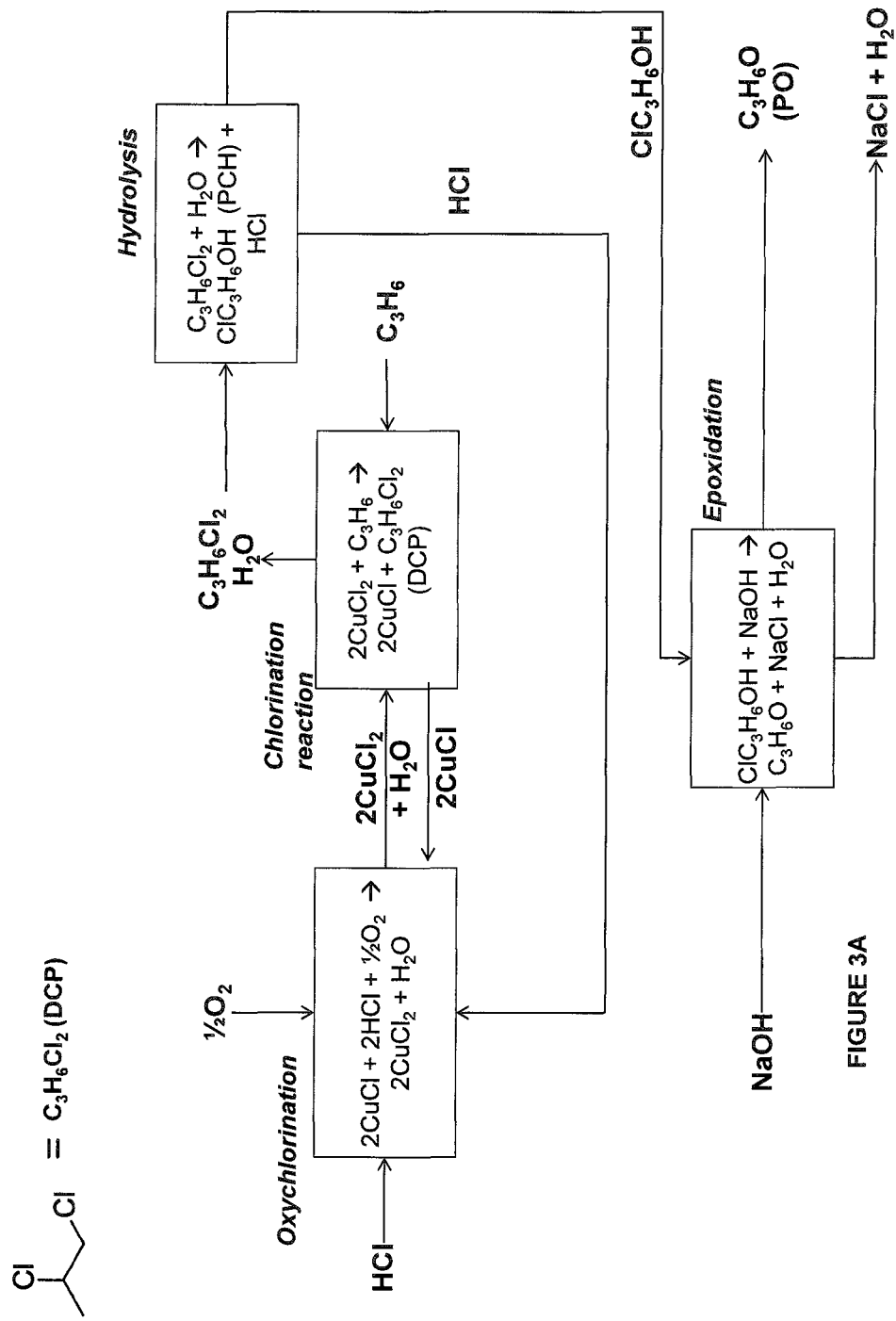
FIG. 3A is an illustration of some embodiments related to the oxychlorination reaction, the chlorination reaction, and the epoxidation reaction using propylene.

In some embodiments of the aspects described herein (as illustrated in FIGS. 1A, 2A, and 3A), the method further comprises an intermediate step of forming one or more products comprising DCP and hydrolyzing the DCP to PCH. In some embodiments, the hydrolysis step is in situ. In some embodiments, the method comprises forming one or more products comprising DCP, separating the one or more products comprising DCP from the metal chloride solution, and hydrolyzing the DCP to PCH. In some embodiments of the above noted method aspect, the PCH is formed directly without the intermediate step of DCP.

Figure 3B:
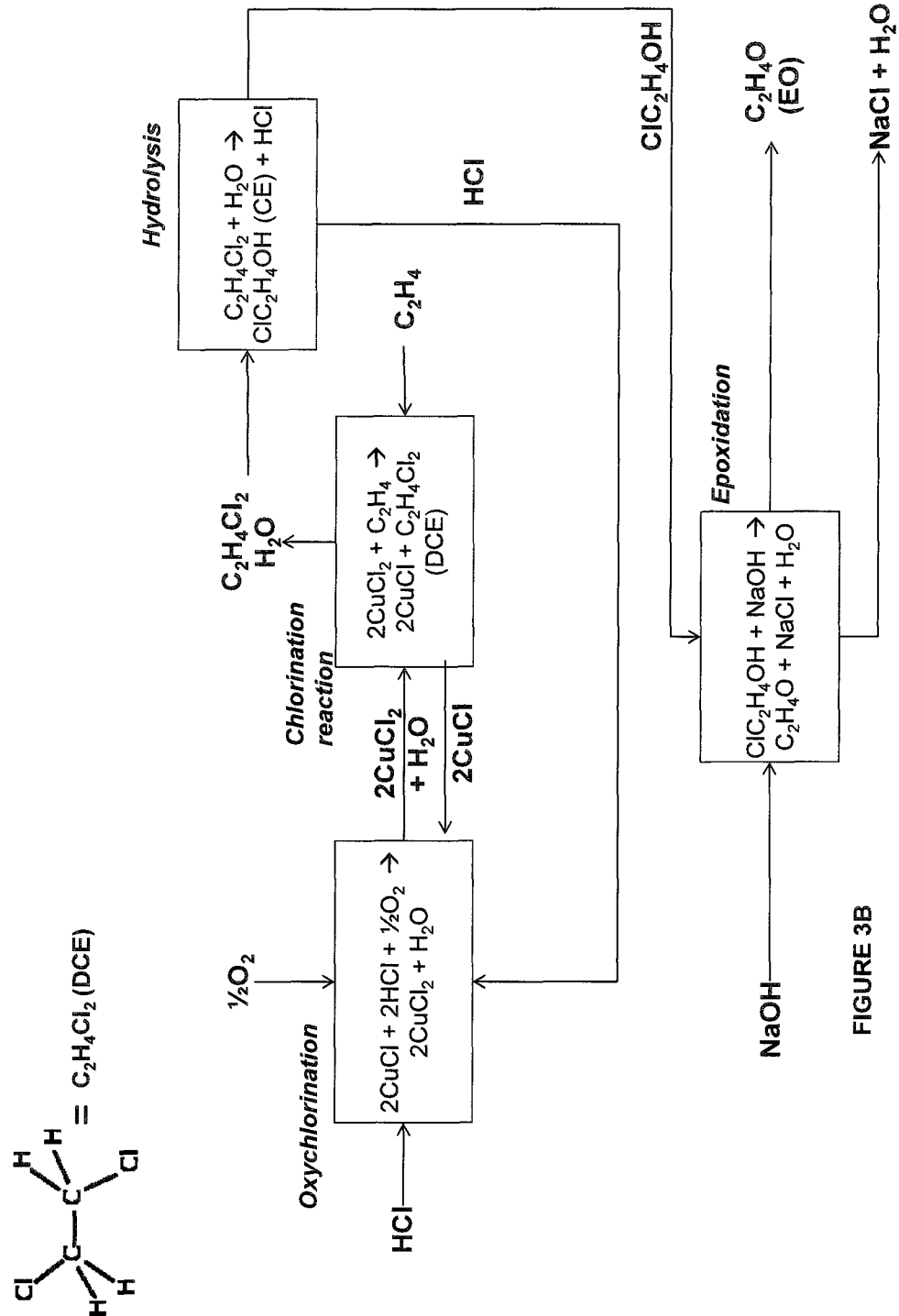
FIG. 3B is an illustration of some embodiments related to the oxychlorination reaction, the chlorination reaction, and the epoxidation reaction using ethylene.

Similarly, in some embodiments of the aspects described herein (as illustrated in FIGS. 1B, 2B, and 3B), the method further comprises an intermediate step of forming one or more products comprising DCE and hydrolyzing the DCE to CE. In some embodiments, the hydrolysis step is in situ. In some embodiments, the method comprises forming one or more products comprising DCE, separating the one or more products comprising DCE from the metal chloride solution, and hydrolyzing the DCE to CE. In some embodiments of the above noted method aspect, the CE is formed directly without the intermediate step of DCE.

In some embodiments, there are provided systems that carry out the above noted method described herein.

In some embodiments, there are provided systems that include an oxychlorination reactor operably connected to a chlorination reactor and configured to oxychlorinate metal chloride with metal ion from lower oxidation state to higher oxidation state in presence of HCl and oxygen;

a chlorination reactor operably connected to the oxychlorination reactor wherein the chlorination reactor is configured to receive the metal chloride with the metal ion in the higher oxidation state from the oxychlorination reactor and chlorinate propylene or ethylene with the metal chloride with the metal ion in the higher oxidation state to result in one or more products comprising PCH or one or more products comprising CE, respectively, and the metal chloride solution with the metal ion in the lower oxidation state; and an epoxide reactor operably connected to the chlorination reactor and configured to epoxidize PCH or CE with a base to form PO or EO, respectively.

In some embodiments of the systems described herein, the system further comprises a hydrolyzing chamber operably connected to the chlorination reactor and configured to receive the DCP or DCE from the chlorination reactor and hydrolyze the DCP to PCH or hydrolyze the DCE to CE. In some embodiments, the hydrolyzing chamber is also operably connected to the epoxide reactor and is configured to transfer PCH or the CE to the epoxide reactor.

In some embodiments of the above noted system, the system further comprises means for transferring HCl formed in the hydrolyzing chamber to the oxychlorination reactor. Such means include any means for transferring liquids including, but not limited to, conduits, tanks, pipes, and the like.

The above noted aspect is illustrated in FIGS. 3A and 3B. The above noted aspect eliminates electrochemical reaction. The method illustrated in FIGS. 3A and 3B, includes formation of DCP or DCE in the chlorination reaction and its subsequent hydrolysis to PCH or CE respectively, in the hydrolysis step. It is to be understood that no DCP or DCE may be formed, and PCH or CE may be formed directly in the chlorination reactor; or DCP or DCE may convert to PCH or CE respectively in situ in the presence of water; or DCP or DCE may be separated and hydrolyzed to PCH or CE respectively as illustrated in FIGS. 3A and 3B. All of these embodiments are well within the scope of the invention. In some embodiments, the HCl produced after hydrolysis is recirculated back to the oxychlorination reaction.

In the method above, caustic may be purchased but would still be only half of the original PCH or CE plant. The above noted process eliminates the chlorine purchase (effectively debottlenecking any processes constrained by chlorine capacity) and cuts the caustic consumption in half. The same amount of propylene or ethylene may still be consumed with a purchase of only one mole of HCl (readily available at most facilities) and half a mole of oxygen ($O_2$). The CapEx for this retrofit may be minimized because there are no cells to purchase.

In some of the above noted aspects and embodiments, the one or more products from propylene further comprise 1,2-dichloropropane (DCP). In some of the above noted aspects and embodiments, the methods further comprise hydrolyzing the DCP to the PCH. In some of the above noted aspects and embodiments, the one or more products from ethylene further comprise 1,2-dichloroethane (DCE). In some of the above noted aspects and embodiments, the methods further comprise hydrolyzing the DCE to the CE.

In one aspect, there is provided a method that includes
(i) contacting chlorine gas with a solution comprising metal chloride and oxidizing the metal chloride with metal ion in a lower oxidation state to a higher oxidation state with the chlorine gas;
(ii) chlorinating propylene with the metal chloride with the metal ion in the higher oxidation state in the solution to result in one or more products comprising propylene chlorohydrin (PCH) and the metal chloride with the metal ion in the lower oxidation state; or chlorinating ethylene with the metal chloride with the metal ion in the higher oxidation state in the solution to result in one or more products comprising chloroethanol (CE) and the metal chloride with the metal ion in the lower oxidation state; and
(iii) epoxidizing the PCH or the CE with a base to form propylene oxide (PO) or ethylene oxide (EO), respectively.

In some embodiments of the above noted aspect, the electrochemical oxidation of CuCl to $CuCl_2$, as illustrated in FIGS. 1A, 1B, 2A, 2B, 5 and 6, may be replaced by oxidation of CuCl to $CuCl_2$ with chlorine gas. For example, in some embodiments, traditional chlor-alkali process producing chlorine gas may be retro-fitted with the chlorination, oxychlorination, and epoxidation reactors of the invention in order to produce PO from propylene or EO from ethylene. For example, in areas where chlorine is used as a feedstock in various downstream processes, the operator may want to continue to produce chlorine in the traditional chlor-alkali electrolyzer and still reap some of the benefits of the processes described herein. In some situations, the operators may save on the investment cost of using the existing chlor-alkali electrolyzer.

In some embodiments, there are provided systems that carry out the above noted methods.

In some embodiments, there are provided systems that include an oxidation reactor configured to oxidize metal chloride with metal ion from lower oxidation state to higher oxidation state in presence of chlorine gas;

a chlorination reactor operably connected to the oxidation reactor wherein the chlorination reactor is configured to receive the metal chloride with the metal ion in the higher oxidation state from the oxidation reactor and chlorinate propylene or ethylene with the metal chloride with the metal ion in the higher oxidation state to result in one or more products comprising PCH or one or more products comprising CE, respectively, and the metal chloride solution with the metal ion in the lower oxidation state; and an epoxide reactor operably connected to the chlorination reactor and configured to epoxidize PCH or CE with a base to form PO or EO, respectively.

In some embodiments, the system further comprises an oxychlorination reactor operably connected to a chlorination reactor and configured to oxychlorinate metal chloride with metal ion from lower oxidation state to higher oxidation state in presence of HCl and oxygen.

In some embodiments of the systems described herein, the one or more products from propylene further comprise DCP. In some embodiments of the systems described herein, the one or more products from ethylene further comprise DCE. In some embodiments of the systems described herein, the system further comprises a hydrolyzing chamber operably connected to the chlorination reactor and configured to receive the DCP or DCE from the chlorination reactor and hydrolyze the DCP to PCH or hydrolyze the DCE to CE. In some embodiments, the hydrolyzing chamber is also operably connected to the epoxide reactor and is configured to transfer PCH or the CE to the epoxide reactor. The oxychlorination reaction/reactor; the hydrolyzing reaction/chamber and epoxide reaction/reactor, have been all described in detail herein.

In some embodiments of the above noted system, the system further comprises means for transferring solutions in between the reactors. Such means include any means for transferring liquids including, but not limited to, conduits, tanks, pipes, and the like.

Figure 4A:
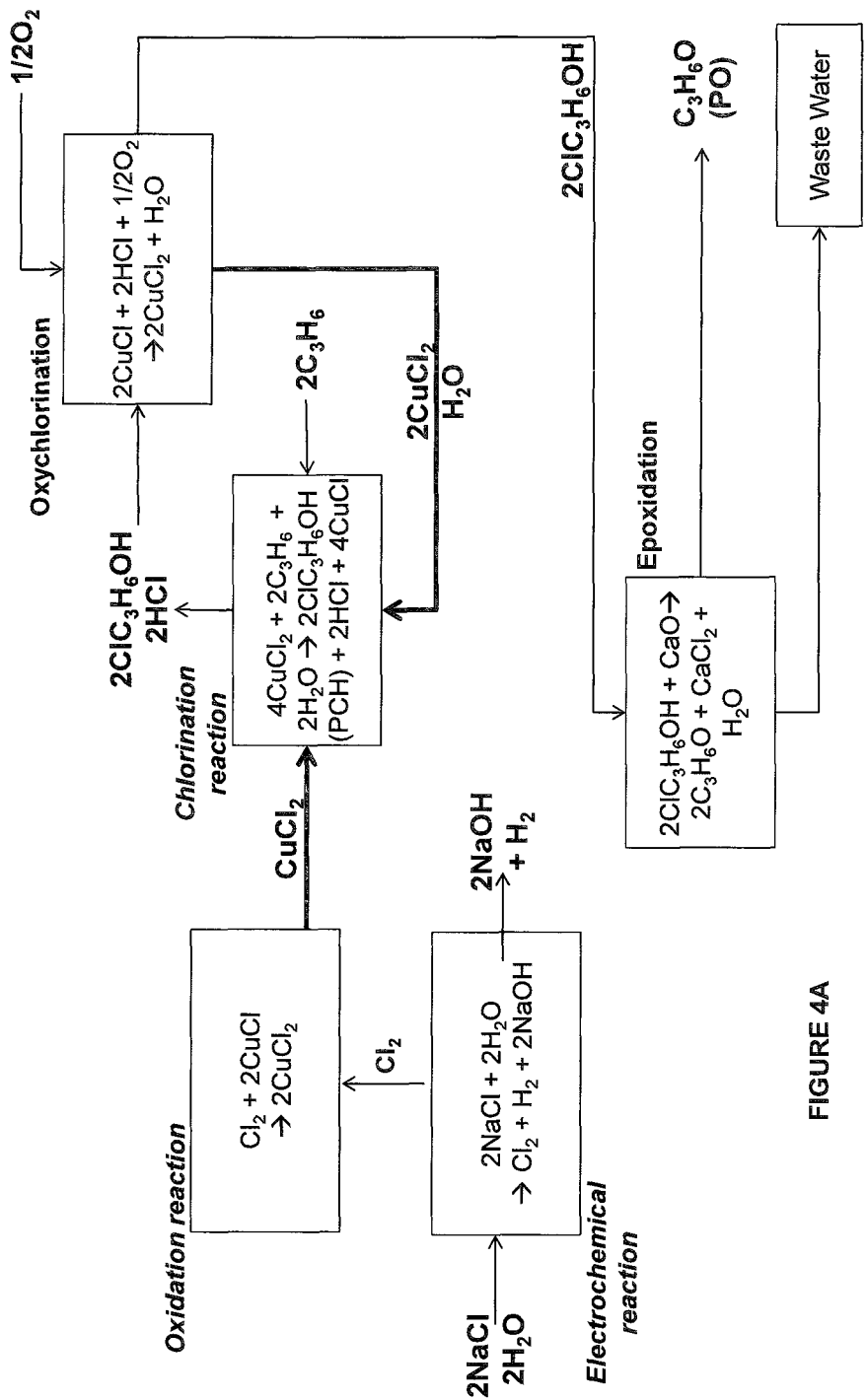
FIG. 4A is an illustration of some embodiments related to the oxidation reaction, the chlorination reaction, oxychlorination reaction, and the epoxidation reaction using propylene.
Figure 4B:
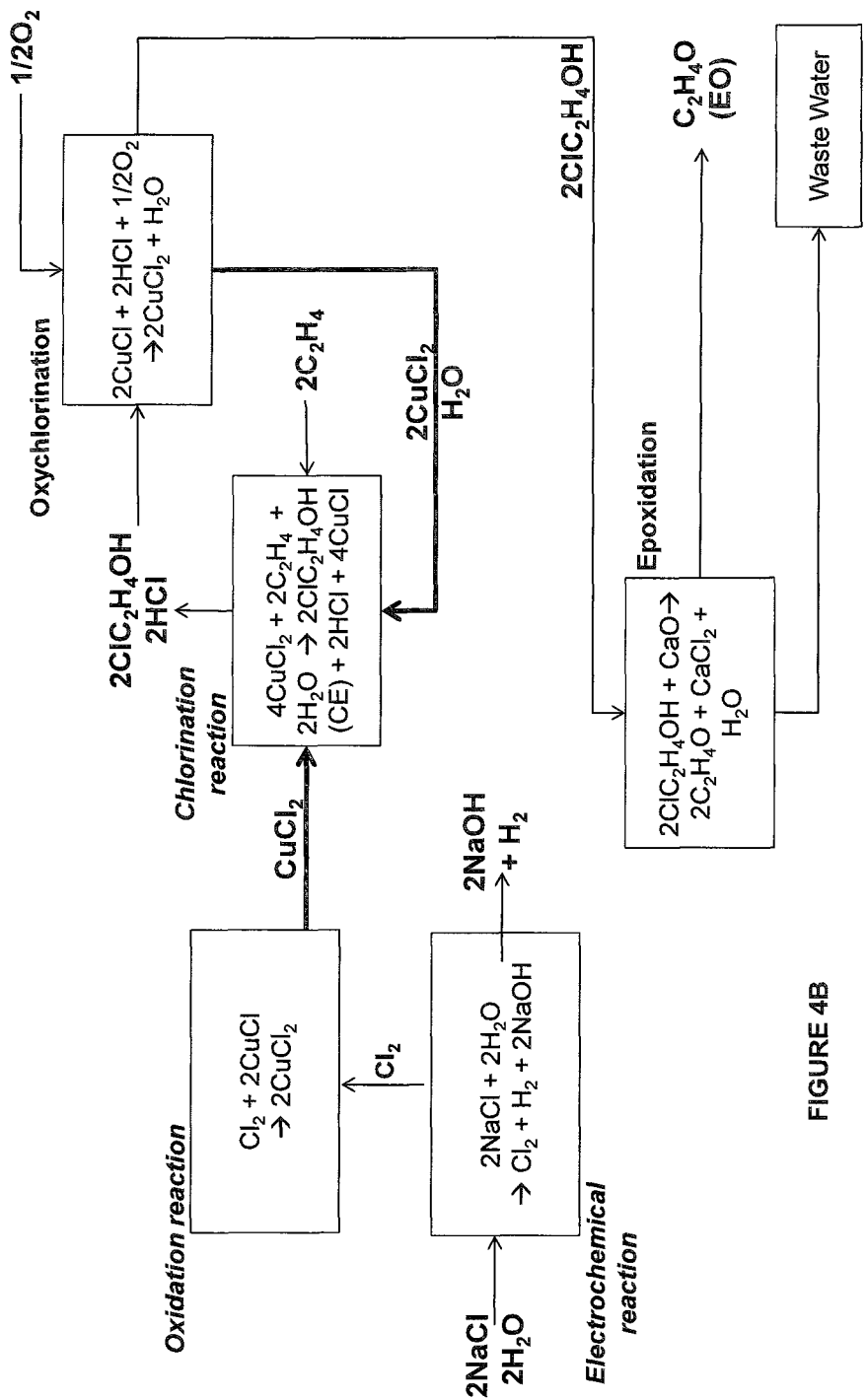
FIG. 4B is an illustration of some embodiments related to the oxidation reaction, the chlorination reaction, oxychlorination reaction, and the epoxidation reaction using ethylene.

The above noted aspect is illustrated in FIGS. 4A and 4B. As explained, the above noted aspect eliminates electrochemical reaction of the invention but replaces it with the chlor-alkali electrolyzer that produces chlorine gas. The methods illustrated in FIGS. 4A and 4B, illustrate the electrochemical reaction of the chlor-alkali electrolyzer that produces NaOH, $H_2$, and $Cl_2$. In the oxidation reactor, the CuCl is converted to $CuCl_2$ by the direct addition of $Cl_2$. This reaction may take place in a slurry reactor or in a liquid phase reactor where gaseous chlorine is injected directly into the liquid or slurry. The outlet of this reactor may feed the chlorination reactor where PCH or CE is generated from propylene or ethylene and $CuCl_2$. The PCH or CE may be then separated from the aqueous stream and sent to the epoxidation reactor. The residual aqueous copper chloride stream (liquid or slurry) then may feed the oxychlorination reactor where CuCl may be converted to $CuCl_2$ via the reaction shown in FIGS. 4A and 4B. The oxychlorination and the epoxidation reactions have been described in detail herein. The chlor-alkali process to form chlorine gas is shown as an illustrative example only; any source of chlorine gas can be used to carry out the methods and systems provided herein.

Depending on the downstream usage, chlorine produced in the chlor-alkali electrolyzer may be dried or may be used directly without drying. In some embodiments, waste HCl from other processes may be provided to the oxychlorination unit. Such chemical processes include, but not limited to, ethylene dichloride (EDC) cracking and phosgene based reactions where HCl may be generated as a by-product.

Although not shown in FIGS. 4A and 4B, the copper chloride stream may be fed from the oxychlorination reactor to the oxidation reactor or vice versa.

In some of the above noted aspects and embodiments, the oxidizing, the chlorinating, and the oxychlorinating steps are all carried out in saltwater.

In some of the above noted aspects and embodiments, the saltwater comprises alkali metal chloride or alkaline earth metal chloride. In some of the above noted aspects and embodiments, the alkali metal chloride is sodium chloride or potassium chloride. Alkali metal chlorides and alkaline earth metal chlorides are well known in the art and are all included in the scope of this application.

In some of the above noted aspects and embodiments, the methods further comprise separating the one or more products from the metal chloride in the saltwater. In some of the above noted aspects and embodiments, the methods further comprise separating the PCH or the CE from the metal chloride in the saltwater. The separation techniques have been described herein.

In some embodiments of the method and system aspects and embodiments provided herein, the concentration of the metal chloride with the metal ion in the lower oxidation state, the concentration of the metal chloride with the metal ion in the higher oxidation state, and the concentration of the salt in the water (e.g. alkali metal chloride), each individually or collectively may affect the performance of each of the electrochemical cell/reaction, oxychlorination reactor/reaction, and chlorination reactor/reaction and also affect the STY (space time yield) and selectivity of PCH or CE. Since the electrochemical cell/reaction, oxychlorination reactor/reaction, and chlorination reactor/reaction are interconnected in various combinations in the present invention, it was found that the concentrations of the metal chloride with lower and higher oxidation state and the salt concentration exiting the systems/reactions and entering the systems/reactions may affect the performance, yield, selectivity, STY, and/or voltage as applicable to the systems.

In some of the above noted aspects and embodiments (as appropriate to the combination), concentration of the metal chloride with the metal ion in the lower oxidation state entering the oxychlorination reaction is between about 0.5-2M; concentration of the metal chloride with the metal ion in the lower oxidation state entering the chlorination reaction is between about 0.1-1.8M; concentration of the metal chloride with the metal ion in the lower oxidation state entering the electrochemical reaction is between about 0.6-2.5M; or combinations thereof.

In some of the above noted aspects and embodiments, the methods further comprise separating the metal chloride solution from the one or more products comprising PCH or CE after the chlorinating step and delivering the metal chloride solution back to the electrochemical reaction and/or the oxychlorination reaction.

In some of the above noted aspects and embodiments, the yield of the PO is more than 90 wt % and/or the space time yield (STY) of the PO is more than 0.1. In some of the above noted aspects and embodiments, the yield of the EO is more than 90 wt % and/or the space time yield (STY) of the EO is more than 0.1.

In some of the above noted aspects and embodiments, the metal chloride with the metal ion in the lower oxidation state is CuCl and the metal chloride with the metal ion in the higher oxidation state is $CuCl_2$.

In some embodiments of the aforementioned aspect, when the electrochemical cell, the chlorination reactor and/or the oxychlorination reactor are operably connected (depending on the combinations described herein) to the other systems, the systems further comprises a conduit or a pipe or a delivery system (fitted with valves etc.) operably connected between the reactors or systems configured to deliver the one or more products, the saltwater and the metal chlorides from one reactor or system to the other. For example, in some embodiments, the system further comprises a conduit or a pipe or a delivery system (fitted with valves etc.) operably connected between the oxychlorination reactor and the chlorination reactor (e.g. in FIGS. 3A and 3B) and configured to deliver the metal chloride solution containing the metal ion in the higher oxidation state and the saltwater of the oxychlorination reactor to the chlorination reactor for the chlorination of the propylene or ethylene to form one or more products.

In some embodiments, the system further comprises a separator operably connected to the chlorination reactor and configured to separate the one or more products from the metal chloride in the saltwater after the chlorination reactor. In some embodiments, the separator is further configured to deliver the metal chloride solution with the metal ion in the lower oxidation state to the electrochemical cell and/or the oxychlorination reactor. In some embodiments, the system further comprises a conduit or a pipe or a delivery system (fitted with valves etc.) operably connected between the chlorination reactor and the electrochemical cell/the oxychlorination reactor and configured to recirculate back the saltwater after the chlorination. Further, in some embodiments, the system further comprises a conduit or a pipe or a delivery system (fitted with valves etc.) operably connected between the oxychlorination reactor or the chlorination reactor and the epoxidation reactor and configured to deliver the PCH or the CE after separation, to the epoxidation reactor for the formation of PO or EO respectively. The examples of conduits include, without limitation, pipes, tubes, tanks, and other means for transferring the liquid solutions. In some embodiments, the conduits attached to the systems also include means for transferring gases such as, but not limited to, pipes, tubes, tanks, and the like. The gases include, for example only, propylene or ethylene to the chlorination reactor, oxygen or ozone gas to the oxychlorination reactor, or the oxygen gas to the cathode chamber of the electrochemical cell etc.

Figure 5:
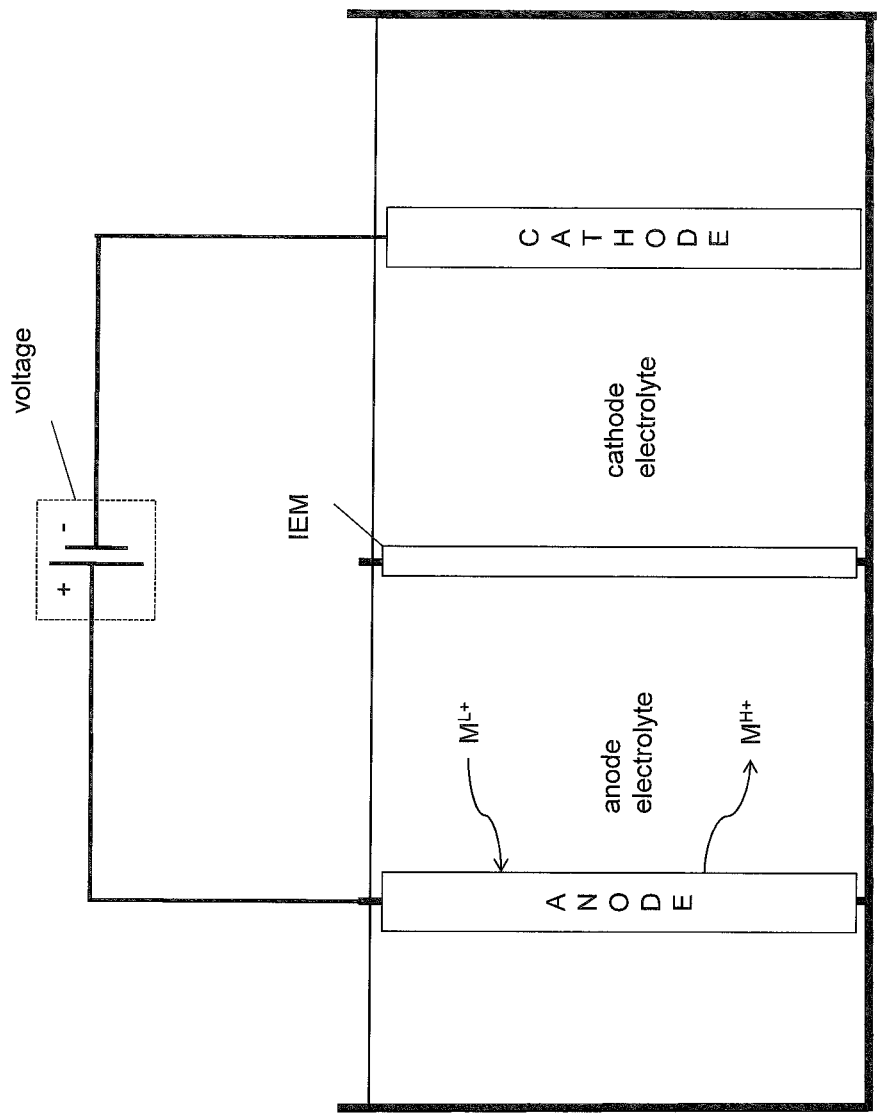
FIG. 5 is an illustration of some embodiments of the electrochemical system.

The electrochemical cell or system may be any electrochemical cell that oxidizes metal ions at the anode. Illustrated in FIG. 5 is an electrochemical system having an anode and a cathode separated by an ion exchange membrane. The anode electrolyte contains metal ions in the lower oxidation state (represented as $M^{L+}$) which are converted by the anode to metal ions in the higher oxidation state (represented as $M^{H+}$). As used herein "lower oxidation state" represented as L+ in $M^{L+}$ includes the lower oxidation state of the metal. For example, lower oxidation state of the metal ion may be 1+, 2+, 3+, 4+, or 5+. As used herein "higher oxidation state" represented as H+ in $M^{H+}$ includes the higher oxidation state of the metal. For example, higher oxidation state of the metal ion may be 2+, 3+, 4+, 5+, or 6+.

Figure 6:
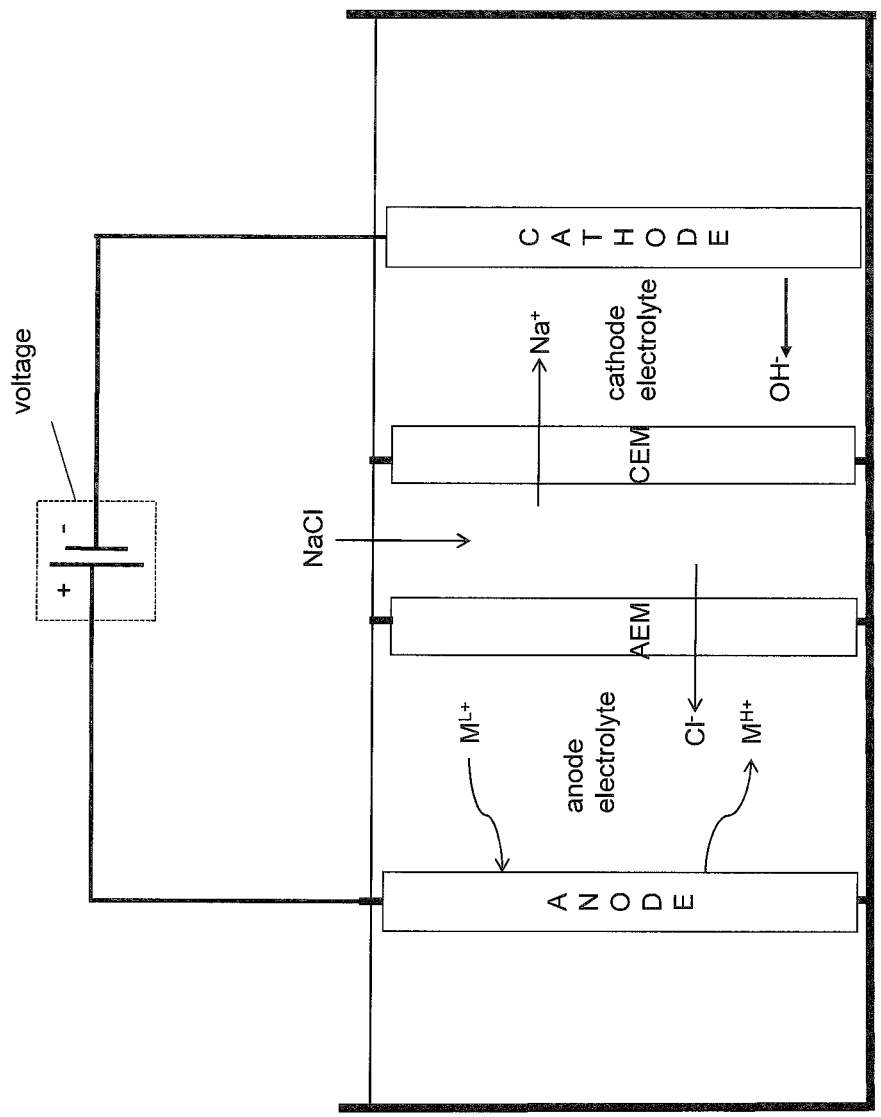
FIG. 6 is an illustration of some embodiments of the electrochemical system.

Illustrated in FIG. 6 is an electrochemical system having an anode and a cathode separated by anion exchange membrane and cation exchange membrane creating a third middle chamber containing a third electrolyte, such as saltwater, e.g. alkali metal chloride or alkaline earth metal chloride including but not limited to, sodium chloride; potassium chloride; lithium chloride; magnesium chloride; calcium chloride; strontium chloride, or barium chloride etc. The anode chamber includes the anode and an anode electrolyte in contact with the anode. In some embodiments, the anode electrolyte comprises saltwater and metal chloride. The saltwater comprises alkali metal ions such as, for example only, alkali metal chloride or alkaline earth metal ions such as, for example only, alkaline earth metal chloride, as described above. The cathode chamber includes the cathode and a cathode electrolyte in contact with the cathode. The cathode electrolyte may also contain saltwater containing alkali metal ions such as, for example only, alkali metal chloride or alkaline earth metal ions such as, for example only, alkaline earth metal chloride, as described above. A combination of the alkali metal chloride and the alkaline earth metal chloride may also be present in anode electrolyte, cathode electrolyte, and/or middle chamber. The cathode electrolyte may also contain alkali metal hydroxide. The metal ion of the metal chloride is oxidized in the anode chamber of the electrochemical cell from the lower oxidation state $M^{L+}$ to the higher oxidation state $M^{H+}$. The electron(s) generated at the anode are used to drive the reaction at the cathode. The cathode reaction may be any reaction known in the art. The anode chamber and the cathode chamber separated by the ion exchange membrane (IEM) allows the passage of ions, such as, but not limited to, sodium ions in some embodiments to the cathode electrolyte if the anode electrolyte comprises saltwater such as, alkali metal ions (in addition to the metal ions such as metal chloride), such as, sodium chloride. The sodium ions combine with hydroxide ions in the cathode electrolyte to form sodium hydroxide. It is to be understood that while the metal ion of the metal chloride is oxidized from the lower to the higher oxidation state (electrochemical and oxychlorination reactions) or reduced from the higher to the lower oxidation state (chlorination reaction) in the systems herein, there always is a mixture of the metal chloride with the metal ion in the lower oxidation state and the higher oxidation state in each of the systems. It is also to be understood that the figures presented herein are for illustration purposes only and only illustrate few modes of the systems. The detailed embodiments of each of the systems are described herein and all the combinations of such detailed embodiments can be combined to carry out the invention.

In the electrochemical cells, cathode reaction may be any reaction that does or does not form an alkali in the cathode chamber. Such cathode consumes electrons and carries out any reaction including, but not limited to, the reaction of water to form hydroxide ions and hydrogen gas or reaction of oxygen gas and water to form hydroxide ions or reduction of protons from an acid such as hydrochloric acid to form hydrogen gas or reaction of protons from hydrochloric acid and oxygen gas to form water. In some embodiments, the electrochemical cells may include production of alkali in the cathode chamber of the cell. The alkali generated in the cathode chamber may be used for epoxidation of PCH to PO, epoxidation of CE to EO, or may be used for neutralization of HCl as described herein.

In the embodiments herein, all the methods/systems including electrochemical, chlorination, and oxychlorination methods/systems comprise metal chloride in saltwater. Various examples of saltwater have been described herein. Further, in the embodiments herein, all the methods/systems including electrochemical, chlorination, and oxychlorination methods/systems comprise metal chloride in lower oxidation state and higher oxidation state in saltwater. For example only, in the embodiments herein, all the methods/systems including electrochemical, chlorination, and oxychlorination methods/systems comprise copper chloride in saltwater. In the embodiments herein, the oxidation of the aqueous solution of the metal chloride with the metal ion oxidized from the lower oxidation state to the higher oxidation state in the electrochemical reaction or the oxychlorination reaction or the reduction of the aqueous solution of the metal chloride with the metal ion reduced from the higher oxidation state to the lower oxidation state in the chlorination reaction is all carried out in the aqueous medium such as saltwater. Examples of saltwater include water comprising alkali metal ions such as alkali metal chloride or alkaline earth metal ions such as alkaline earth metal chloride. Examples include, without limitation, sodium chloride, potassium chloride, lithium chloride, calcium chloride, magnesium chloride etc.

In some embodiments, the temperature of the anode electrolyte in the electrochemical cell/reaction is between 70-90° C., the temperature of the solution in the chlorination reactor/reaction is between 120-200° C., and/or the temperature of the solution in the oxychlorination reactor/reaction is between 70-200° C. depending on the configuration of the electrochemical cell/reaction, the chlorination reactor/reaction, and the oxychlorination reactor/reaction. In some embodiments, the lower temperature of the liquid or liquid/gas phase oxychlorination provided herein as compared to high temperatures of solid/gas phase oxychlorination, may provide economic benefits such as, but not limited to lower capital and operating expenses.

In all the systems provided herein, the solution in and out of the systems may be recirculated multiple times before sending the solution to the next system. For example, when the oxychlorination reactor is operably connected to the chlorination reactor, the saltwater from the oxychlorination reactor may be sent back to the chlorination reactor or is circulated between the oxychlorination and the chlorination reactor before the solution is taken out of the oxychlorination system and sent to the chlorination reactor.

In all the systems provided herein, the use of oxychlorination may be varied with time throughout the day. For example, the oxychlorination may be run during peak power price times as compared to electrochemical reaction thereby reducing the energy use. For example, oxychlorination may be run in the day time while the electrochemical cell may be run in the night time in order to save the cost of energy.

In some embodiments, the saltwater containing the one or more products and the metal chloride may be subjected to washing step which may include rinsing with an organic solvent or passing the organic product through a column to remove the metal ions. In some embodiments, the organic products may be purified by distillation. In the methods and systems provided herein, the separation and/or purification may include one or more of the separation and purification of the organic products from the metal ion solution; the separation and purification of the organic products from each other; and separation and purification of the metal ion in the lower oxidation state from the metal ion in the higher oxidation state, to improve the overall yield of the organic product, improve selectivity of the organic product, improve purity of the organic product, improve efficiency of the systems, improve ease of use of the solutions in the overall process, improve reuse of the metal solution in the electrochemical and reaction process, and to improve the overall economics of the process. Various methods of separation/purification have been described in US Patent Application Publication No. 2015/0038750, filed Jul. 30, 2014, which is incorporated herein by reference in its entirety.

In some embodiments of the foregoing aspects and embodiments, the yield of PCH and PO or of the CE and EO obtained by using one or more aforementioned combinations of the electrochemical method/system, chlorination method/system, oxychlorination method/system, and/or epoxidation method/system is more than 10 wt % yield; or more than 20 wt % yield; or more than 30 wt % yield; or more than 40 wt % yield; or more than 50 wt % yield; or more than 60 wt % yield; or more than 70 wt % yield; or more than 80 wt % yield; or more than 90 wt % yield; or more than 95 wt % yield; or between 20-90 wt % yield; or between 40-90 wt % yield; or between 50-90 wt % yield, or between 50-99 wt % yield.

In some embodiments of the foregoing aspects and embodiments, the STY (space time yield) of PCH and PO or of the CE and EO, obtained by using one or more aforementioned combinations of the electrochemical method/system, chlorination method/system, oxychlorination method/system, and/or epoxidation method/system, is more than 0.1, or more than 0.5, or is 1, or more than 1, or more than 2, or more than 3, or more than 4, or more than 5, or between 0.1-3, or between 0.5-3, or between 0.5-2, or between 0.5-1, or between 3-5, or between 3-6, or between 3-8. As used herein the STY is yield per time unit per reactor volume. For example, the yield of product may be expressed in mol, the time unit in hour and the volume in liter. The volume may be the nominal volume of the reactor, e.g. in a packed bed reactor, the volume of the vessel that holds the packed bed is the volume of the reactor. The STY may also be expressed as STY based on the consumption of propylene or ethylene to form the product. For example only, in some embodiments, the STY of the product may be deduced from the amount of propylene or ethylene consumed during the reaction. The selectivity may be the mol of product/mol of the propylene or ethylene consumed (e.g. only, mol PCH made/mol propylene consumed or mol CE made/mol ethylene consumed). The yield may be the amount of the product isolated. The purity may be the amount of the product/total amount of all products (e.g. only, amount of PCH or CE/all the organic products formed).

The systems provided herein include the reactor that carries out the chlorination, oxychlorination, or the epoxidation. The "reactor" as used herein is any vessel or unit in which the chlorination, oxychlorination, or epoxidation reaction provided herein, is carried out. The chlorination reactor is configured to contact the metal chloride in the anode electrolyte or the metal chloride in the saltwater from the oxychlorination reaction, with propylene or ethylene to form the one or more products. The oxychlorination reactor is configured to contact the metal chloride with the metal ion in the lower oxidation state with the oxidant to form the metal chloride with the metal ion in the higher oxidation state. The reactor may be any means for contacting the contents as mentioned above. Such means or such reactor are well known in the art and include, but not limited to, pipe, column, duct, tank, series of tanks, container, tower, conduit, and the like. The reactor may be equipped with one or more of controllers to control temperature sensor, pressure sensor, control mechanisms, inert gas injector, etc. to monitor, control, and/or facilitate the reaction.

In some embodiments, the reactor system may be a series of reactors connected to each other. The reaction vessel may be a stirred tank. The stirring may increase the mass transfer rate of propylene or ethylene into the aqueous anolyte phase accelerating the reaction to form the one or more products. The reactors for the chlorination reaction as well as the oxychlorination reaction need to be made of material that is compatible with the aqueous or the saltwater streams containing metal ions flowing between the systems. In some embodiments, the electrochemical system, the chlorination reactor and/or the oxychlorination reactor are made of corrosion resistant materials that are compatible with metal ion containing water, such materials include, titanium, steel etc.

The reactor effluent gases may be quenched with water in the prestressed (e.g., brick-lined) packed tower. The liquid leaving the tower maybe cooled further and separated into the aqueous phase and organic phase. The aqueous phase may be split part being recycled to the tower as quench water and the remainder may be recycled to the reactor or the electrochemical system. The organic product may be cooled further and flashed to separate out more water and dissolved propylene or ethylene. This dissolved propylene or ethylene may be recycled back to the reactor. The uncondensed gases from the quench tower may be recycled to the reactor, except for the purge stream to remove inerts. The purge stream may go through the propylene or ethylene recovery system to keep the over-all utilization of propylene or ethylene high, e.g., as high as 95%. Experimental determinations may be made of flammability limits for propylene or ethylene gas at actual process temperature, pressure and compositions. The construction material of the plant or the systems may include prestressed brick linings, Hastealloys B and C, inconel, dopant grade titanium (e.g. AKOT, Grade II), tantalum, Kynar, Teflon, PEEK, glass, or other polymers or plastics. The reactor may also be designed to continuously flow the anode electrolyte in and out of the reactor.

In some embodiments, the reaction between the metal chloride with metal ion in higher oxidation state and propylene or ethylene is carried out in the reactor provided herein under reaction conditions including, but not limited to, the temperature of between 120-200° C. or between 120-175° C. or between 150-185° C. or between 150-175° C.; pressure of between 100-500 psig or between 100-400 psig or between 100-300 psig or between 150-350 psig or between 200-300 psig, or combinations thereof depending on the desired product. The reactor provided herein is configured to operate at the temperature of between 120-200° C. or between 120-185° C. or between 150-200° C. or between 150-175° C.; pressure of between 100-500 psig or between 100-400 psig or between 100-300 psig or between 150-350 psig or between 200-300 psig, or combinations thereof depending on the desired product. In some embodiments, the reactor provided herein may operate under reaction conditions including, but not limited to, the temperature and pressure in the range of between 135-180° C., or between 135-175° C., or between 140-180° C., or between 140-170° C., or between 140-160° C., or between 150-180° C., or between 150-170° C., or between 150-160° C., or between 155-165° C., or 140° C., or 150° C., or 160° C., or 170° C. and 200-300 psig depending on the desired product. In some embodiments, the reactor provided herein may operate under reaction conditions including, but not limited to, the temperature and pressure in the range of between 135-180° C., or between 135-175° C., or between 140-180° C., or between 140-170° C., or between 140-160° C., or between 150-180° C. and 200-300 psig depending on the desired product.

One or more of the reaction conditions include, such as, but not limited to, temperature of the chlorination mixture, incubation time, total chloride concentration in the chlorination mixture, and/or concentration of the metal chloride in the higher oxidation state can be set to assure high selectivity, high yield, and/or high STY operation.

Reaction heat may be removed by vaporizing water or by using heat exchange units. In some embodiments, a cooling surface may not be required in the reactor and thus no temperature gradients or close temperature control may be needed.

In some embodiments, the systems may include one reactor or a series of multiple reactors connected to each other or operating separately. The reactor may be a packed bed such as, but not limited to, a hollow tube, pipe, column or other vessel filled with packing material. The reactor may be a trickle-bed reactor. In some embodiments, the packed bed reactor includes a reactor configured such that the aqueous medium containing the metal ions and propylene or ethylene flow counter-currently in the reactor or includes the reactor where the saltwater containing the metal ions flows in from the top of the reactor and the propylene or ethylene gas is pressured in from the bottom at e.g., but not limited to, 200 psi or above, such as, for example, 250 psi, 300 psi or 600 psi. In some embodiments, in the latter case, the propylene or ethylene gas may be pressured in such a way that only when the propylene or ethylene gas gets consumed and the pressure drops, that more propylene or ethylene gas flows into the reactor. The trickle-bed reactor includes a reactor where the saltwater containing the metal ions and propylene or ethylene flow co-currently in the reactor. In some embodiments, the reactor may be a tray column or a spray tower. Any of the configurations of the reactor described herein may be used to carry out the methods of the invention.

Efficient chlorination may be dependent upon achieving intimate contact between the feedstock and the metal ion in solution and the chlorination reaction may be carried out by a technique designed to improve or maximize such contact. The metal ion solution may be agitated by stirring or shaking or any desired technique, e.g. the reaction may be carried out in a column, such as a packed column, or a trickle-bed reactor or reactors described herein. For example, where propylene or ethylene is gaseous, a counter-current technique may be employed wherein the propylene or ethylene is passed upwardly through a column or reactor and the metal ion solution is passed downwardly through the column or reactor. In addition to enhancing contact of the propylene or ethylene and the metal ion in the solution, the techniques described herein may also enhance the rate of dissolution of the propylene or ethylene in the solution, as may be desirable in the case where the solution is aqueous and the water-solubility of the propylene or ethylene is low. Dissolution of the feedstock may also be assisted by higher pressures.

A variety of packing material of various shapes, sizes, structure, wetting characteristics, form, and the like may be used in the packed bed or trickle bed reactor, described herein. The packing material includes, but not limited to, polymer (e.g. only Teflon PTFE), ceramic, glass, metal, natural (wood or bark), or combinations thereof. In some embodiments, the packing can be structured packing or loose or unstructured or random packing or combination thereof. The structured packing includes unflowable corrugated metal plates or gauzes. In some embodiments, the structured packing material individually or in stacks fits fully in the diameter of the reactor. The unstructured packing or loose packing or random packing includes flow able void filling packing material.

Examples of loose or unstructured or random packing material include, but not limited to, Raschig rings (such as in ceramic material), pall rings (e.g. in metal and plastic), lessing rings, Michael Bialecki rings (e.g. in metal), berl saddles, intalox saddles (e.g. in ceramic), super intalox saddles, Tellerette® ring (e.g. spiral shape in polymeric material), etc.

Examples of structured packing material include, but not limited to, thin corrugated metal plates or gauzes (honeycomb structures) in different shapes with a specific surface area. The structured packing material may be used as a ring or a layer or a stack of rings or layers that have diameter that may fit into the diameter of the reactor. The ring may be an individual ring or a stack of rings fully filling the reactor. In some embodiments, the voids left out by the structured packing in the reactor are filled with the unstructured packing material.

Examples of structured packing material includes, without limitation, Flexipac®, Intalox®, Flexipac® HC®, etc. In a structured packing material, corrugated sheets may be arranged in a crisscross pattern to create flow channels for the vapor phase. The intersections of the corrugated sheets may create mixing points for the liquid and vapor phases. The structured packing material may be rotated about the column (reactor) axis to provide cross mixing and spreading of the vapor and liquid streams in all directions. The structured packing material may be used in various corrugation sizes and the packing configuration may be optimized to attain the highest efficiency, capacity, and pressure drop requirements of the reactor. The structured packing material may be made of a material of construction including, but not limited to, titanium, stainless steel alloys, carbon steel, aluminum, nickel alloys, copper alloys, zirconium, thermoplastic, etc. The corrugation crimp in the structured packing material may be of any size, including, but not limited to, Y designated packing having an inclination angle of 45° from the horizontal or X designated packing having an inclination angle of 60° from the horizontal. The X packing may provide a lower pressure drop per theoretical stage for the same surface area. The specific surface area of the structured packing may be between 50-800 $m^2/m^3$; or between 75-350 $m^2/m^3$; or between 200-800 $m^2/m^3$; or between 150-800 $m^2/m^3$; or between 500-800 $m^2/m^3$.

In some embodiments, the structured or the unstructured packing material as described above is used in the distillation or flash column described herein for separation and purification of the products.

All the electrochemical and reactor systems and methods described herein are carried out in more than 5 wt % water or more than 6 wt % water or saltwater. The saltwater has been described herein.

The electrochemical cells in the methods and systems provided herein are membrane electrolyzers. The electrochemical cell may be a single cell or may be a stack of cells connected in series or in parallel. The electrochemical cell may be a stack of 5 or 6 or 50 or 100 or more electrolyzers connected in series or in parallel. Each cell comprises an anode, a cathode, and an ion exchange membrane.

In some embodiments, the electrolyzers provided herein are monopolar electrolyzers. In the monopolar electrolyzers, the electrodes may be connected in parallel where all anodes and all cathodes are connected in parallel. In such monopolar electrolyzers, the operation takes place at high amperage and low voltage. In some embodiments, the electrolyzers provided herein are bipolar electrolyzers. In the bipolar electrolyzers, the electrodes may be connected in series where all anodes and all cathodes are connected in series. In such bipolar electrolyzers, the operation takes place at low amperage and high voltage. In some embodiments, the electrolyzers are a combination of monopolar and bipolar electrolyzers and may be called hybrid electrolyzers.

In some embodiments of the bipolar electrolyzers as described above, the cells are stacked serially constituting the overall electrolyzer and are electrically connected in two ways. In bipolar electrolyzers, a single plate, called bipolar plate, may serve as base plate for both the cathode and anode. The electrolyte solution may be hydraulically connected through common manifolds and collectors internal to the cell stack. The stack may be compressed externally to seal all frames and plates against each other which are typically referred to as a filter press design. In some embodiments, the bipolar electrolyzer may also be designed as a series of cells, individually sealed, and electrically connected through back-to-back contact, typically known as a single element design. The single element design may also be connected in parallel in which case it would be a monopolar electrolyzer.

In some embodiments, the cell size may be denoted by the active area dimensions. In some embodiments, the active area of the electrolyzers used herein may range from 0.5-1.5 meters tall and 0.4-3 meters wide. The individual compartment thicknesses may range from 0.5 mm-50 mm.

The electrolyzers used in the methods and systems provided herein, are made from corrosion resistant materials. Variety of materials was tested in metal solutions such as copper and at varying temperatures, for corrosion testing. The materials include, but not limited to, polyvinylidene fluoride, viton, polyether ether ketone, fluorinated ethylene propylene, fiber-reinforced plastic, halar, ultem (PEI), perfluoroalkoxy, tefzel, tyvar, fibre-reinforced plastic-coated with derakane 441-400 resin, graphite, akot, tantalum, hastelloy C2000, titanium Gr.7, titanium Gr.2, or combinations thereof. In some embodiments, these materials can be used for making the electrochemical cells and/or it components including, but not limited to, tank materials, piping, heat exchangers, pumps, reactors, cell housings, cell frames, electrodes, instrumentation, valves, and all other balance of plant materials. In some embodiments, the material used for making the electrochemical cell and its components include, but not limited to, titanium Gr.2.

The "metal ion" or "metal" or "metal ion of the metal chloride" as used herein, includes any metal ion capable of being converted from lower oxidation state to higher oxidation state. Examples of metal ions in the corresponding metal chloride include, but not limited to, iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof. In some embodiments, the metal ions in the corresponding metal chloride include, but not limited to, iron, copper, tin, chromium, or combination thereof. In some embodiments, the metal ion in the corresponding metal chloride is copper. In some embodiments, the metal ion in the corresponding metal chloride is tin. In some embodiments, the metal ion in the corresponding metal chloride is iron. In some embodiments, the metal ion in the corresponding metal chloride is chromium. In some embodiments, the metal ion in the corresponding metal chloride is platinum. The "oxidation state" as used herein, includes degree of oxidation of an atom in a substance. For example, in some embodiments, the oxidation state is the net charge on the ion. Some examples of the reaction of the metal ions at the anode are as shown in Table I below (SHE is standard hydrogen electrode). The theoretical values of the anode potential are also shown. It is to be understood that some variation from these voltages may occur depending on conditions, pH, concentrations of the electrolytes, etc and such variations are well within the scope of the invention.

TABLE I

| Anode Reaction | Anode Potential (V vs. SHE) |
| --- | --- |
| $Ag^+ \rightarrow Ag^{2+} + e^-$ | −1.98 |
| $Co^{2+} \rightarrow Co^{3+} + e^-$ | −1.82 |
| $Pb^{2+} \rightarrow Pb^{4+} + 2e^-$ | −1.69 |
| $Ce^{3+} \rightarrow Ce^{4+} + e^-$ | −1.44 |
| $2Cr^{3+} + 7H_2O \rightarrow Cr_2O_7^{2-} + 14H^+ + 6e^-$ | −1.33 |
| $Tl^+ \rightarrow Tl^{3+} + 2e^-$ | −1.25 |
| $Hg_2^{2+} \rightarrow 2Hg^{2+} + 2e^-$ | −0.91 |
| $Fe^{2+} \rightarrow Fe^{3+} + e^-$ | −0.77 |
| $V^{3+} + H_2O \rightarrow VO^{2+} + 2H^+ + e^-$ | −0.34 |
| $U^{4+} + 2H_2O \rightarrow UO_2^{2+} + 4H^+ + e^-$ | −0.27 |
| $Bi^+ \rightarrow Bi^{3+} + 2e^-$ | −0.20 |
| $Ti^{3+} + H_2O \rightarrow TiO^{2+} + 2H^+ + e^-$ | −0.19 |
| $Cu^+ \rightarrow Cu^{2+} + e^-$ | −0.16 |
| $UO_2^+ \rightarrow UO_2^{2+} + e^-$ | −0.16 |
| $Sn^{2+} \rightarrow Sn^{4+} + 2e^-$ | −0.15 |
| $Ru(NH_3)_6^{2+} \rightarrow Ru(NH_3)_6^{3+} + e^-$ | −0.10 |
| $V^{2+} \rightarrow V^{3+} + e^-$ | +0.26 |
| $Eu^{2+} \rightarrow Eu^{3+} + e^-$ | +0.35 |
| $Cr^{2+} \rightarrow Cr^{3+} + e^-$ | +0.42 |
| $U^{3+} \rightarrow U^{4+} + e^-$ | +0.52 |

The metal chloride may be present as a compound of the metal or an alloy of the metal or combination thereof. In some embodiments, the anion attached to the metal is same as the anion of the electrolyte. For example, for sodium or potassium chloride used as an electrolyte, a metal chloride, such as, but not limited to, iron chloride, copper chloride, tin chloride, chromium chloride etc. is used as the metal compound. In such embodiments, it may be desirable to have sufficient concentration of chloride ions in the electrolyte to dissolve the metal salt but not high enough to cause undesirable ionic speciation.

In some embodiments, the metal ions of the metal chloride used in the electrochemical systems described herein, may be chosen based on the solubility of the metal in the anode electrolyte and/or cell voltages desired for the metal oxidation from the lower oxidation state to the higher oxidation state.

It is to be understood that the metal chloride with the metal ion in the lower oxidation state and the metal chloride with the metal ion in the higher oxidation state are both present in the anode electrolyte. The anode electrolyte exiting the anode chamber contains higher amount of the metal chloride in the higher oxidation state than the amount of the metal chloride in the higher oxidation state entering the anode chamber. Owing to the oxidation of the metal chloride from the lower oxidation state to the higher oxidation state at the anode, the ratio of the metal chloride in the lower and the higher oxidation state is different in the anode electrolyte entering the anode chamber and exiting the anode chamber. Suitable ratios of the metal ion in the lower and higher oxidation state in the anode electrolyte have been described herein. The mixed metal ion in the lower oxidation state with the metal ion in the higher oxidation state may assist in lower voltages in the electrochemical systems and high yield and selectivity in corresponding chlorination reaction with the propylene or ethylene.

In some embodiments, the metal ion in the anode electrolyte is a mixed metal ion. For example, the anode electrolyte containing the copper ion in the lower oxidation state and the copper ion in the higher oxidation state may also contain another metal ion such as, but not limited to, iron. In some embodiments, the presence of a second metal ion in the anode electrolyte may be beneficial in lowering the total energy of the electrochemical reaction in combination with the catalytic reaction.

Some examples of the metal compounds or metal chloride that may be used in the systems and methods of the invention include, but are not limited to, copper (I) chloride, iron (II) chloride, tin (II) chloride, chromium (II) chloride, zinc (II) chloride, etc.

In some embodiments, the anode may contain a corrosion stable, electrically conductive base support. Such as, but not limited to, amorphous carbon, such as carbon black, fluorinated carbons like the specifically fluorinated carbons described in U.S. Pat. No. 4,908,198 and available under the trademark SFC™ carbons. Other examples of electrically conductive base materials include, but not limited to, sub-stoichiometric titanium oxides, such as, Magneli phase sub-stoichiometric titanium oxides having the formula $TiO_x$ wherein x ranges from about 1.67 to about 1.9. Some examples of titanium sub-oxides include, without limitation, titanium oxide $Ti_4O_7$. The electrically conductive base materials also include, without limitation, metal titanates such as $M_xTi_yO_z$ such as $M_xTi_4O_7$, etc. In some embodiments, carbon based materials provide a mechanical support or as blending materials to enhance electrical conductivity but may not be used as catalyst support to prevent corrosion.

In some embodiments, the anode is not coated with an electrocatalyst. In some embodiments, the anode is made of an electro conductive base metal such as titanium coated with or without electrocatalysts. Some examples of electrically conductive base materials include, but not limited to, sub-stoichiometric titanium oxides, such as, Magneli phase sub-stoichiometric titanium oxides having the formula $TiO_x$ wherein x ranges from about 1.67 to about 1.9. Some examples of titanium sub-oxides include, without limitation, titanium oxide $Ti_4O_7$. The electrically conductive base materials also include, without limitation, metal titanates such as $M_xTi_yO_z$ such as $M_xTi_4O_7$, etc. Examples of electrocatalysts have been described herein and include, but not limited to, highly dispersed metals or alloys of the platinum group metals, such as platinum, palladium, ruthenium, rhodium, iridium, or their combinations such as platinum-rhodium, platinum-ruthenium, titanium mesh coated with PtIr mixed metal oxide or titanium coated with galvanized platinum; electrocatalytic metal oxides, such as, but not limited to, $IrO_2$; gold, tantalum, carbon, graphite, organometallic macrocyclic compounds, and other electrocatalysts well known in the art. The electrodes may be coated with electrocatalysts using processes well known in the art.

In some embodiments, the electrodes described herein, relate to porous homogeneous composite structures as well as heterogeneous, layered type composite structures wherein each layer may have a distinct physical and compositional make-up, e.g. porosity and electroconductive base to prevent flooding, and loss of the three phase interface, and resulting electrode performance.

In some embodiments, the electrodes provided herein may include anodes and cathodes having porous polymeric layers on or adjacent to the anolyte or catholyte solution side of the electrode which may assist in decreasing penetration and electrode fouling. Stable polymeric resins or films may be included in a composite electrode layer adjacent to the anolyte comprising resins formed from non-ionic polymers, such as polystyrene, polyvinyl chloride, polysulfone, etc., or ionic-type charged polymers like those formed from polystyrenesulfonic acid, sulfonated copolymers of styrene and vinylbenzene, carboxylated polymer derivatives, sulfonated or carboxylated polymers having partially or totally fluorinated hydrocarbon chains and aminated polymers like polyvinylpyridine. Stable microporous polymer films may also be included on the dry side to inhibit electrolyte penetration. In some embodiments, the gas-diffusion cathodes includes such cathodes known in the art that are coated with high surface area coatings of precious metals such as gold and/or silver, precious metal alloys, nickel, and the like.

Any of the cathodes provided herein can be used in combination with any of the anodes described above. In some embodiments, the cathode used in the electrochemical systems of the invention, is a hydrogen gas producing cathode.

Following are the reactions that take place at the cathode and the anode:

$$H_2O + e^- \rightarrow 1/2 H_2 + OH^- \text{ (cathode)}$$

$$M^{L+} \rightarrow M^{H+} + xe^- \text{(anode where } x=1\text{-}3\text{)}$$

For example, $Fe^{2+} \rightarrow Fe^{3+} + e^-$ (anode)

$Cr^{2+} \rightarrow Cr^{3+} + e^-$ (anode)

$Sn^{2+} \rightarrow Sn^{4+} + 2e^-$ (anode)

$Cu^+ \rightarrow Cu^{2+} + e^-$ (anode)

The hydrogen gas formed at the cathode may be vented out or captured and stored for commercial purposes. The $M^{H+}$ formed at the anode combines with chloride ions to form metal chloride in the higher oxidation state such as, but not limited to, $FeCl_3$, $CrCl_3$, $SnCl_4$, or $CuCl_2$ etc. The hydroxide ion formed at the cathode combines with sodium ions to form sodium hydroxide. In some embodiments, the cathode used in the electrochemical systems of the invention, is a hydrogen gas producing cathode that does not form an alkali. Following are the reactions that take place at the cathode and the anode:

$$2H^+ + 2e^- \rightarrow H_2 \text{ (cathode)}$$

$$M^{L+} \rightarrow M^{H+} + xe^- \text{(anode where } x=1\text{-}3\text{)}$$

For example, $Fe^{2+} \rightarrow Fe^{3+} + e^-$ (anode)

$Cr^{2+} \rightarrow Cr^{3+} + e^-$ (anode)

$Sn^{2+} \rightarrow Sn^{4+} + 2e^-$ (anode)

$Cu^+ \rightarrow Cu^{2+} + e^-$ (anode)

The hydrogen gas may be vented out or captured and stored for commercial purposes. The $M^{H+}$ formed at the anode combines with chloride ions to form metal chloride in the higher oxidation state such as, but not limited to, $FeCl_3$, $CrCl_3$, $SnCl_4$, or $CuCl_2$ etc.

In some embodiments, the cathode in the electrochemical systems of the invention may be a gas-diffusion cathode. In some embodiments, the cathode in the electrochemical systems of the invention may be a gas-diffusion cathode forming an alkali at the cathode. As used herein, the "gas-diffusion cathode," or "gas-diffusion electrode," or other equivalents thereof include any electrode capable of reacting a gas to form ionic species. In some embodiments, the gas-diffusion cathode, as used herein, is an oxygen depolarized cathode (ODC). Such gas-diffusion cathode may be called gas-diffusion electrode, oxygen consuming cathode, oxygen reducing cathode, oxygen breathing cathode, oxygen depolarized cathode, and the like.

Following are the reactions that may take place at the anode and the cathode.

$H_2O + 1/2 O_2 + 2e^- \rightarrow 2OH^-$ (cathode)

$M^{L+} \rightarrow M^{H+} + xe^-$ (anode where x=1-3)

For example, $2Fe^{2+} \rightarrow 2Fe^{3+} + e^-$ (anode)

$2Cr^{2+} \rightarrow 2Cr^{3+} + 2e^-$ (anode)

$Sn^{2+} \rightarrow Sn^{4+} + 2e^-$ (anode)

$2Cu^+ \rightarrow 2Cu^{2+} + 2e^-$ (anode)

The $M^{H+}$ formed at the anode combines with chloride ions to form metal chloride $MCl_n$ such as, but not limited to, $FeCl_3$, $CrCl_3$, $SnCl_4$, or $CuCl_2$ etc. The hydroxide ion formed at the cathode reacts with sodium ions to form sodium hydroxide. The oxygen at the cathode may be atmospheric air or any commercial available source of oxygen.

The methods and systems containing the gas-diffusion cathode or the ODC, as described herein may result in voltage savings as compared to methods and systems that include the hydrogen gas producing cathode. The voltage savings in-turn may result in less electricity consumption and less carbon dioxide emission for electricity generation.

While the methods and systems containing the gas-diffusion cathode or the ODC result in voltage savings as compared to methods and systems containing the hydrogen gas producing cathode, both the systems i.e. systems containing the ODC and the systems containing hydrogen gas producing cathode of the invention, show significant voltage savings as compared to chlor-alkali system conventionally known in the art. The voltage savings in-turn may result in less electricity consumption and less carbon dioxide emission for electricity generation. In some embodiments, the electrochemical system of the invention (2 or 3-compartment cells with hydrogen gas producing cathode or ODC) has a theoretical voltage savings of more than 0.5V, or more than 1V, or more than 1.5V, or between 0.5-3V, as compared to chlor-alkali process. In some embodiments, this voltage saving is achieved with a cathode electrolyte pH of between 7-15, or between 7-14, or between 6-12, or between 7-12, or between 7-10.

In some embodiments, the cathode in the electrochemical systems of the invention may be a gas-diffusion cathode that reacts HCl and oxygen gas to form water.

Following are the reactions that may take place at the anode and the cathode.

$2H^+ + 1/2 O_2 + 2e^- \rightarrow H_2O$ (cathode)

$M^{L+} \rightarrow M^{H+} + xe^-$ (anode where x=1-3)

For example, $2Fe^{2+} \rightarrow 2Fe^{3+} + 2e^-$ (anode)

$2Cr^{2+} \rightarrow 2Cr^{3+} + 2e^-$ (anode)

$Sn^{2+} \rightarrow Sn^{4+} + 2e^-$ (anode)

$2Cu^+ \rightarrow 2Cu^{2+} + 2e^-$ (anode)

The $M^{H+}$ formed at the anode combines with chloride ions to form metal chloride $MCl_n$ such as, but not limited to, $FeCl_3$, $CrCl_3$, $SnCl_4$, or $CuCl_2$ etc. The oxygen at the cathode may be atmospheric air or any commercial available source of oxygen.

The cathode electrolyte containing the alkali maybe withdrawn from the cathode chamber. The purity of the alkali formed in the methods and systems may vary depending on the end use requirements. For example, methods and systems provided herein that use an electrochemical cell equipped with membranes may form a membrane quality alkali which may be substantially free of impurities. In some embodiments, a less pure alkali may also be formed by avoiding the use of membranes. In some embodiments, the alkali may be separated from the cathode electrolyte using techniques known in the art, including but not limited to, diffusion dialysis. In some embodiments, the alkali formed in the cathode electrolyte is more than 2% w/w or more than 5% w/w or between 5-50% w/w.

In some embodiments, the cathode electrolyte and the anode electrolyte are separated in part or in full by an ion exchange membrane. In some embodiments, the ion exchange membrane is an anion exchange membrane or a cation exchange membrane. In some embodiments, the cation exchange membranes in the electrochemical cell, as disclosed herein, are conventional and are available from, for example, Asahi Kasei of Tokyo, Japan; or from Membrane International of Glen Rock, N.J., or DuPont, in the USA. Examples of CEM include, but are not limited to, N2030WX (Dupont), F8020/F8080 (Flemion), and F6801 (Aciplex). CEMs that are desirable in the methods and systems of the invention have minimal resistance loss, greater than 90% selectivity, and high stability in concentrated caustic. AEMs, in the methods and systems of the invention are exposed to concentrated metallic salt anolytes and saturated brine stream. It is desirable for the AEM to allow passage of salt ion such as chloride ion to the anolyte but reject the metallic ion species from the anolyte.

In some embodiments, the AEM used in the methods and systems provided herein, is also substantially resistant to the organic compounds such that AEM does not interact with the organics and/or the AEM does not react or absorb metal ions. In some embodiments, this can be achieved, for example only, by using a polymer that does not contain a free radical or anion available for reaction with organics or with metal ions. For example only, a fully quarternized amine containing polymer may be used as an AEM.

Examples of cationic exchange membranes include, but not limited to, cationic membrane consisting of a perfluorinated polymer containing anionic groups, for example sulphonic and/or carboxylic groups. However, it may be appreciated that in some embodiments, depending on the need to restrict or allow migration of a specific cation or an anion species between the electrolytes, a cation exchange membrane that is more restrictive and thus allows migration of one species of cations while restricting the migration of another species of cations may be used as, e.g., a cation exchange membrane that allows migration of sodium ions into the cathode electrolyte from the anode electrolyte while restricting migration of other ions from the anode electrolyte into the cathode electrolyte, may be used. Similarly, in some embodiments, depending on the need to restrict or allow migration of a specific anion species between the electrolytes, an anion exchange membrane that is more restrictive and thus allows migration of one species of anions while restricting the migration of another species of anions may be used as, e.g., an anion exchange membrane that allows migration of chloride ions into the anode electrolyte from the cathode electrolyte while restricting migration of hydroxide ions from the cathode electrolyte into the anode electrolyte, may be used. Such restrictive cation exchange membranes are commercially available and can be selected by one ordinarily skilled in the art.

In some embodiments, the membranes may be selected such that they can function in an acidic and/or basic electrolytic solution as appropriate. Other desirable characteristics of the membranes include high ion selectivity, low ionic resistance, high burst strength, and high stability in an acidic electrolytic solution in a temperature range of room temperature to 150° C. or higher, or a alkaline solution in similar temperature range may be used. In some embodiments, it is desirable that the ion exchange membrane prevents the transport of the metal ion from the anolyte to the catholyte. In some embodiments, a membrane that is stable in the range of 0° C. to 150° C.; 0° C. to 90° C.; or 0° C. to 80° C.; or 0° C. to 70° C.; or 0° C. to 60° C.; or 0° C. to 50° C.; or 0° C. to 40° C., or 0° C. to 30° C., or 0° C. to 20° C., or 0° C. to 10° C., or higher may be used. For other embodiments, it may be useful to utilize an ion-specific ion exchange membranes that allows migration of one type of cation but not another; or migration of one type of anion and not another, to achieve a desired product or products in an electrolyte. In some embodiments, the membrane may be stable and functional for a desirable length of time in the system, e.g., several days, weeks or months or years at temperatures in the range of 0° C. to 90° C. In some embodiments, for example, the membranes may be stable and functional for at least 1 day, at least 5 days, 10 days, 15 days, 20 days, 100 days, 1000 days, 5-10 years, or more in electrolyte temperatures at 100° C., 90° C., 80° C., 70° C., 60° C., 50° C., 40° C., 30° C., 20° C., 10° C., 5° C. and more or less.

The ohmic resistance of the membranes may affect the voltage drop across the anode and cathode, e.g., as the ohmic resistance of the membranes increase, the voltage across the anode and cathode may increase, and vice versa. Membranes that can be used include, but are not limited to, membranes with relatively low ohmic resistance and relatively high ionic mobility; and membranes with relatively high hydration characteristics that increase with temperatures, and thus decreasing the ohmic resistance. By selecting membranes with lower ohmic resistance known in the art, the voltage drop across the anode and the cathode at a specified temperature can be lowered.

In some embodiments, the aqueous electrolyte including the catholyte or the cathode electrolyte and/or the anolyte or the anode electrolyte, or the third electrolyte disposed between AEM and CEM, in the systems and methods provided herein include, but not limited to, saltwater or fresh water. The saltwater has been described herein. "Saltwater" as used herein includes its conventional sense to refer to a number of different types of aqueous fluids other than fresh water, where the saltwater includes, but is not limited to, water containing alkali metal ions such as, alkali metal chlorides e.g. sodium chloride, potassium chloride, water containing alkaline earth metal ions such as, alkaline earth metal chlorides e.g. calcium chloride, brackish water, sea water and brine (including, naturally occurring subterranean brines or anthropogenic subterranean brines and man-made brines, e.g., geothermal plant wastewaters, desalination waste waters, etc), as well as other salines having a salinity that is greater than that of freshwater. Brine is water saturated or nearly saturated with salt and has a salinity that is 50 ppt (parts per thousand) or greater. In some embodiments, the depleted saltwater withdrawn from the electrochemical cells is replenished with salt and re-circulated back in the electrochemical cell.

In some embodiments, the electrolyte including the cathode electrolyte and/or the anode electrolyte and/or the third electrolyte, such as, saltwater includes water containing alkali metal chloride or alkaline earth metal chloride of more than 1% chloride content, such as, NaCl; or more than 10% NaCl; or more than 25% NaCl; or more than 50% NaCl; or more than 70% NaCl; or between 1-99% NaCl; or between 1-70% NaCl; or between 1-50% NaCl; or between 1-25% NaCl; or between 1-10% NaCl; or between 10-99% NaCl; or between 10-50% NaCl; or between 20-99% NaCl; or between 20-50% NaCl; or between 30-99% NaCl; or between 30-50% NaCl; or between 40-99% NaCl; or between 40-50% NaCl; or between 50-90% NaCl; or between 60-99% NaCl; or between 70-99% NaCl; or between 80-99% NaCl; or between 90-99% NaCl; or between 90-95% NaCl. The percentages recited herein include wt % or wt/wt % or wt/v %.

In some embodiments, the cathode electrolyte, such as, saltwater, fresh water, and/or sodium hydroxide do not include alkaline earth metal ions or divalent cations. As used herein, the divalent cations include alkaline earth metal ions, such as but not limited to, calcium, magnesium, barium, strontium, radium, etc. In some embodiments, the cathode electrolyte, such as, saltwater, fresh water, and/or sodium hydroxide include less than 1% w/w divalent cations. In some embodiments, the cathode electrolyte, such as, seawater, freshwater, brine, brackish water, and/or sodium hydroxide include less than 1% w/w divalent cations including, but not limited to, calcium, magnesium, and combination thereof.

The amount of the alkali metal or alkaline earth metal ions added to the anode electrolyte may be between 0.01-5M; between 0.01-4M; or between 0.01-3M; or between 0.01-2M; or between 0.01-1M; or between 1-5M; or between 1-4M; or between 1-3M; or between 1-2M; or between 2-5M; or between 2-4M; or between 2-3M; or between 3-5M.

In some embodiments of the methods and systems described herein, the anode electrolyte may contain an acid. The acid may be added to the anode electrolyte to bring the pH of the anolyte to 1 or 2 or less. The acid may be hydrochloric acid or sulfuric acid.

In some embodiments, the electrolyte in the electrochemical systems and methods described herein include the aqueous medium containing more than 5 wt % water. In some embodiments, the aqueous medium includes more than 5 wt % water; or more than 5.5 wt % water; or more than 6 wt %; or more than 20 wt % water; or more than 25 wt % water;

or more than 50 wt % water. In some embodiments, the aqueous medium may comprise a water soluble organic solvent.

In some embodiments of the methods and systems described herein, the amount of total metal ion in the anode electrolyte or the amount of metal chloride in the anode electrolyte or the amount of copper chloride in the anode electrolyte or the amount of iron chloride in the anode electrolyte or the amount of chromium chloride in the anode electrolyte or the amount of tin chloride in the anode electrolyte or the amount of platinum chloride or the amount of metal ion that is contacted with propylene or the amount of total metal ion and the alkali metal ions (salt) in the anode electrolyte is between 1-12M; or between 1-11M; or between 1-10M; or between 1-9M; or between 1-8M; or between 1-7M; or between 1-6M; or between 1-5M; or between 1-4M; or between 1-3M; or between 1-2M; or between 2-12M; or between 2-11M; or between 2-10M; or between 2-9M; or between 2-8M; or between 2-7M; or between 2-6M; or between 2-5M; or between 2-4M; or between 2-3M; or between 3-12M; or between 3-11M; or between 3-10M; or between 3-9M; or between 3-8M; or between 3-7M; or between 3-6M; or between 3-5M; or between 3-4M; or between 4-12M; or between 4-11M; or between 4-10M; or between 4-9M; or between 4-8M; or between 4-7M; or between 4-6M; or between 4-5M; or between 5-12M; or between 5-11M; or between 5-10M; or between 5-9M; or between 5-8M; or between 5-7M; or between 5-6M; or between 6-13M; or between 6-12M; or between 6-11M; or between 6-10M; or between 6-9M; or between 6-8M; or between 6-7M; or between 7-12M; or between 7-11M; or between 7-10M; or between 7-9M; or between 7-8M; or between 8-12M; or between 8-11M; or between 8-10M; or between 8-9M; or between 9-12M; or between 9-11M; or between 9-10M; or between 10-12M; or between 10-11M; or between 11-12M. In some embodiments, the amount of total ion in the anode electrolyte, as described above, is the amount of the metal ion in the lower oxidation state plus the amount of the metal ion in the higher oxidation state plus the alkali metal chloride or alkaline earth metal chloride; or the total amount of the metal ion in the higher oxidation state; or the total amount of the metal ion in the lower oxidation state.

In some embodiments, the depleted saltwater from the cell may be circulated back to the cell. In some embodiments, the cathode electrolyte includes 1-90%; 1-50%; or 1-40%; or 1-30%; or 1-15%; or 1-20%; or 1-10%; or 5-90%; or 5-50%; or 5-40%; or 5-30%; or 5-20%; or 5-10%; or 10-90%; or 10-50%; or 10-40%; or 10-30%; or 10-20%; or 15-20%; or 15-30%; or 20-30%, of the sodium hydroxide solution. In some embodiments, the anode electrolyte includes 1-5M; or 1-4.5M; or 1-4M; or 1-3.5M; or 1-3M; or 1-2.5M; or 1-2M; or 1-1.5M; or 2-5M; or 2-4.5M; or 2-4M; or 2-3.5M; or 2-3M; or 2-2.5M; or 3-5M; or 3-4.5M; or 3-4M; or 3-3.5M; or 4-5M; or 4.5-6M metal ion solution. In some embodiments, the anode does not form an oxygen gas. In some embodiments, the anode does not form a chlorine gas.

Depending on the degree of alkalinity desired in the cathode electrolyte, the pH of the cathode electrolyte may be adjusted and in some embodiments is maintained between 6 and 12; or between 7 and 14 or greater; or between 7 and 13; or between 7 and 12; or between 7 and 11; or between 10 and 14 or greater; or between 10 and 13; or between 10 and 12; or between 10 and 11. In some embodiments, the pH of the cathode electrolyte may be adjusted to any value between 7 and 14 or greater, a pH less than 12, a pH 7.0, 7.5, 8.0, 8.5, 9.0, 9.5, 10.0, 10.5, 11.0, 11.5, 12.0, 12.5, 13.0, 13.5, 14.0, and/or greater.

Similarly, in some embodiments of the system, the pH of the anode electrolyte is adjusted and is maintained between 0-7; or between 0-6; or between 0-5; or between 0-4; or between 0-3; or between 0-2; or between 0-1. As the voltage across the anode and cathode may be dependent on several factors including the difference in pH between the anode electrolyte and the cathode electrolyte (as can be determined by the Nernst equation well known in the art), in some embodiments, the pH of the anode electrolyte may be adjusted to a value between 0 and 7, including 0, 0.5, 1.0, 1.5, 2.0, 2.5, 3.0, 3.5, 4.0, 4.5, 5.0, 5.5, 6.0, 6.5 and 7, depending on the desired operating voltage across the anode and cathode. Thus, in equivalent systems, where it is desired to reduce the energy used and/or the voltage across the anode and cathode, e.g., as in the chlor-alkali process, the carbon dioxide or a solution containing dissolved carbon dioxide can be added to the cathode electrolyte to achieve a desired pH difference between the anode electrolyte and cathode electrolyte.

In some embodiments, the systems provided herein result in low to zero voltage systems that generate alkali as compared to chlor-alkali process or chlor-alkali process with ODC or any other process that oxidizes metal ions from lower oxidation state to the higher oxidation state in the anode chamber. In some embodiments, the electrochemical systems described herein run at voltage of less than 2.8V; or less than 2.5V; or less than 2V; or less than 1.2V; or less than 1.1V; or less than 1V; or less than 0.9V; or less than 0.8V; or less than 0.7V; or less than 0.6V; or less than 0.5V; or less than 0.4V; or less than 0.3V; or less than 0.2V; or less than 0.1V; or at zero volts; or between 0-1.2V; or between 0-1V; or between 0-0.5 V; or between 0.5-1V; or between 0.5-2V; or between 0-0.1 V; or between 0.1-1V; or between 0.1-2V; or between 0.01-0.5V; or between 0.01-1.2V; or between 1-1.2V; or between 0.2-1V; or 0V; or 0.5V; or 0.6V; or 0.7V; or 0.8V; or 0.9V; or 1V.

As used herein, the "voltage" includes a voltage or a bias applied to or drawn from an electrochemical cell that drives a desired reaction between the anode and the cathode in the electrochemical cell. In some embodiments, the desired reaction may be the electron transfer between the anode and the cathode such that an alkaline solution, water, or hydrogen gas is formed in the cathode electrolyte and the metal ion is oxidized at the anode. In some embodiments, the desired reaction may be the electron transfer between the anode and the cathode such that the metal ion in the higher oxidation state is formed in the anode electrolyte from the metal ion in the lower oxidation state. The voltage may be applied to the electrochemical cell by any means for applying the current across the anode and the cathode of the electrochemical cell. Such means are well known in the art and include, without limitation, devices, such as, electrical power source, fuel cell, device powered by sun light, device powered by wind, and combination thereof. The type of electrical power source to provide the current can be any power source known to one skilled in the art. For example, in some embodiments, the voltage may be applied by connecting the anodes and the cathodes of the cell to an external direct current (DC) power source. The power source can be an alternating current (AC) rectified into DC. The DC power source may have an adjustable voltage and current to apply a requisite amount of the voltage to the electrochemical cell.

In some embodiments, the current applied to the electrochemical cell is at least 50 mA/cm$^2$; or at least 100 mA/cm$^2$; or at least 150 mA/cm$^2$; or at least 200 mA/cm$^2$; or at least 500 mA/cm$^2$; or at least 1000 mA/cm$^2$; or at least 1500 mA/cm$^2$; or at least 2000 mA/cm$^2$; or at least 2500 mA/cm$^2$; or between 100-2500 mA/cm$^2$; or between 100-2000 mA/cm$^2$; or between 100-1500 mA/cm$^2$; or between 100-1000 mA/cm$^2$; or between 100-500 mA/cm$^2$; or between 200-2500 mA/cm$^2$; or between 200-2000 mA/cm$^2$; or between 200-1500 mA/cm$^2$; or between 200-1000 mA/cm$^2$; or between 200-500 mA/cm$^2$; or between 500-2500 mA/cm$^2$; or between 500-2000 mA/cm$^2$; or between 500-1500 mA/cm$^2$; or between 500-1000 mA/cm$^2$; or between 1000-2500 mA/cm$^2$; or between 1000-2000 mA/cm$^2$; or between 1000-1500 mA/cm$^2$; or between 1500-2500 mA/cm$^2$; or between 1500-2000 mA/cm$^2$; or between 2000-2500 mA/cm$^2$.

In some embodiments, the cell runs at voltage of between 0-3V when the applied current is 100-250 mA/cm$^2$ or 100-150 mA/cm$^2$ or 100-200 mA/cm$^2$ or 100-300 mA/cm$^2$ or 100-400 mA/cm$^2$ or 100-500 mA/cm$^2$ or 150-200 mA/cm$^2$ or 200-150 mA/cm$^2$ or 200-300 mA/cm$^2$ or 200-400 mA/cm$^2$ or 200-500 mA/cm$^2$ or 150 mA/cm$^2$ or 200 mA/cm$^2$ or 300 mA/cm$^2$ or 400 mA/cm$^2$ or 500 mA/cm$^2$ or 600 mA/cm$^2$. In some embodiments, the cell runs at between 0-1V. In some embodiments, the cell runs at between 0-1.5V when the applied current is 100-250 mA/cm$^2$ or 100-150 mA/cm$^2$ or 150-200 mA/cm$^2$ or 150 mA/cm$^2$ or 200 mA/cm$^2$. In some embodiments, the cell runs at between 0-1V at an amperic load of 100-250 mA/cm$^2$ or 100-150 mA/cm$^2$ or 150-200 mA/cm$^2$ or 150 mA/cm$^2$ or 200 mA/cm$^2$. In some embodiments, the cell runs at 0.5V at a current or an amperic load of 100-250 mA/cm$^2$ or 100-150 mA/cm$^2$ or 150-200 mA/cm$^2$ or 150 mA/cm$^2$ or 200 mA/cm$^2$.

The systems provided herein are applicable to or can be used for any of one or more methods described herein. In some embodiments, the systems provided herein further include an oxygen gas supply or delivery system operably connected to the cathode chamber. The oxygen gas delivery system is configured to provide oxygen gas to the gas-diffusion cathode. In some embodiments, the oxygen gas delivery system is configured to deliver gas to the gas-diffusion cathode where reduction of the gas is catalyzed to hydroxide ions. In some embodiments, the oxygen gas and water are reduced to hydroxide ions; un-reacted oxygen gas in the system is recovered; and re-circulated to the cathode. The oxygen gas may be supplied to the cathode using any means for directing the oxygen gas from the external source to the cathode. Such means for directing the oxygen gas from the external source to the cathode or the oxygen gas delivery system are well known in the art and include, but not limited to, pipe, duct, conduit, and the like. In some embodiments, the system or the oxygen gas delivery system includes a duct that directs the oxygen gas from the external source to the cathode. It is to be understood that the oxygen gas may be directed to the cathode from the bottom of the cell, top of the cell or sideways. In some embodiments, the oxygen gas is directed to the back side of the cathode where the oxygen gas is not in direct contact with the catholyte. In some embodiments, the oxygen gas may be directed to the cathode through multiple entry ports. The source of oxygen that provides oxygen gas to the gas-diffusion cathode, in the methods and systems provided herein, includes any source of oxygen known in the art. Such sources include, without limitation, ambient air, commercial grade oxygen gas from cylinders, oxygen gas obtained by fractional distillation of liquefied air, oxygen gas obtained by passing air through a bed of zeolites, oxygen gas obtained from electrolysis of water, oxygen obtained by forcing air through ceramic membranes based on zirconium dioxides by either high pressure or electric current, chemical oxygen generators, oxygen gas as a liquid in insulated tankers, or combination thereof. In some embodiments, the oxygen from the source of oxygen gas may be purified before being administered to the cathode chamber. In some embodiments, the oxygen from the source of oxygen gas is used as is in the cathode chamber.

In some embodiments, the reactor and/or separator components in the systems of the invention may include a control station, configured to control the amount of propylene introduced into the chlorination reactor, the amount of the anode electrolyte introduced into the chlorination or the oxychlorination reactor, the amount of the water containing the organics and the metal ions into the separator, the temperature and pressure conditions in the reactor and the separator, the flow rate in and out of the reactor and the separator, the time and the flow rate of the water going back to the electrochemical cell, etc.

The control station may include a set of valves or multi-valve systems which are manually, mechanically or digitally controlled, or may employ any other convenient flow regulator protocol. In some instances, the control station may include a computer interface, (where regulation is computer-assisted or is entirely controlled by computer) configured to provide a user with input and output parameters to control the amount and conditions, as described above.

The methods and systems of the invention may also include one or more detectors configured for monitoring the flow of propylene or the concentration of the metal ion in the aqueous medium/water/saltwater or the concentration of the organics in the aqueous medium/water/saltwater, etc. Monitoring may include, but is not limited to, collecting data about the pressure, temperature and composition of the aqueous medium and gases. The detectors may be any convenient device configured to monitor, for example, pressure sensors (e.g., electromagnetic pressure sensors, potentiometric pressure sensors, etc.), temperature sensors (resistance temperature detectors, thermocouples, gas thermometers, thermistors, pyrometers, infrared radiation sensors, etc.), volume sensors (e.g., geophysical diffraction tomography, X-ray tomography, hydroacoustic surveyers, etc.), and devices for determining chemical makeup of the aqueous medium or the gas (e.g, IR spectrometer, NMR spectrometer, UV-vis spectrophotometer, high performance liquid chromatographs, inductively coupled plasma emission spectrometers, inductively coupled plasma mass spectrometers, ion chromatographs, X-ray diffractometers, gas chromatographs, gas chromatography-mass spectrometers, flow-injection analysis, scintillation counters, acidimetric titration, and flame emission spectrometers, etc.).

In some embodiments, detectors may also include a computer interface which is configured to provide a user with the collected data about the aqueous medium, metal ions and/or the products. For example, a detector may determine the concentration of the aqueous medium, metal ions and/or the products and the computer interface may provide a summary of the changes in the composition within the aqueous medium, metal ions and/or the products over time. In some embodiments, the summary may be stored as a computer readable data file or may be printed out as a user readable document.

In some embodiments, the detector may be a monitoring device such that it can collect real-time data (e.g., internal pressure, temperature, etc.) about the aqueous medium, metal ions and/or the products. In other embodiments, the detector may be one or more detectors configured to determine the parameters of the aqueous medium, metal ions and/or the products at regular intervals, e.g., determining the composition every 1 minute, every 5 minutes, every 10 minutes, every 30 minutes, every 60 minutes, every 100 minutes, every 200 minutes, every 500 minutes, or some other interval.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Various modifications of the invention in addition to those described herein will become apparent to those skilled in the art from the foregoing description and accompanying figures. Such modifications fall within the scope of the appended claims. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In the examples and elsewhere, some of the abbreviations have the following meanings:

| | |
|---|---|
| AEM = | anion exchange membrane |
| g = | gram |
| HCl = | hydrochloric acid |
| h or hr = | hour |
| l or L = | liter |
| M = | molar |
| kA/m$^2$ = | kiloamps/meter square |
| mg = | milligram |
| min = | minute |
| ml = | milliliter |
| mV = | millivolt |
| NaCl = | sodium chloride |
| NaOH = | sodium hydroxide |
| psi = | pounds per square inch |
| psig = | pounds per square inch guage |
| STY = | space time yield |
| V = | voltage |

EXAMPLES

Example 1

Formation of Dichloropropane from Propylene Using Copper Chloride

This experiment is directed to the formation of 1,2-dichloropropane (DCP) from propylene using cupric chloride. The experiment was conducted in a pressure vessel. The pressure vessel contained an outer jacket containing the catalyst, i.e. cupric chloride solution and an inlet for bubbling propylene gas in the cupric chloride solution. A 150 mL solution of 5M CuCl$_2$, 0.5M CuCl, 1M NaCl, and 0.03M HCl was placed into a glass-lined 450 mL stirred pressure vessel. After purging the closed container with N$_2$, it was heated to 160° C. After reaching this temperature, propylene was added to the container to raise the pressure from the autogenous pressure, mostly owing from water vapor, to a pressure of 130 psig. After 15 minutes, more propylene was added to raise the pressure from 120 psig to 140 psig. After an additional 15 minutes, the pressure was 135 psig. At this time, the reactor was cooled to 14° C., depressurized, and opened. Ethyl acetate was used to rinse the reactor parts and then was used as the extraction solvent. The product was analyzed by gas chromatography which showed 0.203 g of 1,2-dichloropropane that was recovered in the ethyl acetate phase.

Example 2

Electrochemical Reaction

This example illustrates the electrochemical reaction when the corrugated anode and PK membrane was used in the electrochemical cell. The cell configuration on the 40 cm$^2$ active area lab cell was of Ti-base corrugation bridged with coated Ti mesh anode, Ni flynet meshed cathode with platinum group metal catalyst coating, FAA-3-PK-30 anion exchange membrane (FuMA-Tech), and N2030 cation exchange membrane (Dupont). The cell conditions were an anolyte composed of 4.5 M CuCl$_2$, 1.5M CuCl, 2.5M NaCl, a brine feed of 300 g/NaCl at a pH of 2, and a catholyte of 30 wt % sodium hydroxide. The operating temperature of the cell was 90° C. The run time for the electrochemical reaction was 30 min. These conditions achieved conversion of CuCl to CuCl$_2$ at a cell voltage of 2.35V at 3 kA/m$^2$.

Example 3

Oxychlorination Reaction with Varying Cu(I) Concentrations

This example illustrates oxychlorination of the metal chloride from the lower oxidation state to the higher oxidation state. Various anolyte compositions shown in Table I below were weighed into de-ionized water and placed into split-septa glass vials.

TABLE I

| | Initial Compositions | | | |
|---|---|---|---|---|
| Sample | 1 | 2 | 3 | 4 |
| Cu(I) [M] | 0.5 | 1.0 | 1.5 | 1.0 |
| Cu(II) [M] | 5.5 | 5.5 | 5.5 | 5.5 |
| NaCl [M] | 2.5 | 2.5 | 2.5 | 3.0 |

For Cu(I) and Cu(II), the initial materials were CuCl and CuCl$_2$ respectively. The compositions were then oxidized in a parallel, high-throughput reactor system. The reaction atmosphere was clean, dry air at a pressure of 250 psig and the reaction temperature was approximately 160° C. Reaction time was either 30 min. or 60 min. After the reaction was completed, the reaction contents were cooled to ambient temperature and the resulting solutions were titrated for Cu(II) and total copper concentrations by standard literature techniques. The final Cu(I) concentration was then calculated by difference.

To account for the loss of water through the split septa during the experiment, the final Cu(I) concentration was renormalized based on the ratio of the initial total copper concentration and the (higher) final copper concentration. The change in copper concentration was then calculated directly. Where multiple measurements were taken, the results shown below represent the average measurement. The results are as follows in Table II.

TABLE II

| Sample | 1 | | 2 | | 3 | | 4 | |
|---|---|---|---|---|---|---|---|---|
| Initial Cu(I) [M] | 0.5 | | 1.0 | | 1.5 | | 1.0 | |
| Time (minutes) | 30 | 60 | 30 | 60 | 30 | 60 | 30 | 60 |
| Cu(I) Reacted [M] | 0.263 | 0.380 | 0.772 | 0.878 | 0.978 | 1.296 | 0.865 | 0.874 |

In each case, the results show that the amount of Cu(I) oxidized increases with the initial concentration of Cu(I) and the reaction time, as expected. The results also indicate that the presence of additional chloride (in this case in the form of NaCl) accelerates the conversion of CuCl at least at reaction time of 30 minutes.

Example 4

Oxychlorination Reaction with Varying HCl Concentrations, Temperature, and Pressure Kinetic experiments were run in a high throughput system (HTS), that held up to eight sample vials and allowed heating and pressurizing them simultaneously. With anolyte containing 1M CuCl, 5MCuCl2, and 2M NaCl, time series experiments at three different HCl levels and three different (T, p) set-points were conducted. Samples were prepared in duplicate and analyzed via cerium titration in duplicate as well.

The vials were filled with the aforementioned anolyte and a stir-bar was placed in each vial. They were capped and placed in an appropriate tray. For open vial experiments, their septa were slit to allow pressurization and depressurization. For closed vial experiments, at least one open vial filled with water was placed in the tray to ensure equal pressure inside and outside of the vials. The tray was placed in the bottom half of a clamp-shell-reactor and sealed with an o-ring against the top half. The reactor was secured with ten bolts, placed upon a heated stir-plate and covered with an insulating cover. For open vial experiments, pressure was supplied from an air cylinder.

After a set reaction time, the reactor was placed on an aluminum heat sink and rapidly cooled down first with water and from 100° C. downwards with ice. Samples were prepared for either titration or extraction.

Figure 7:
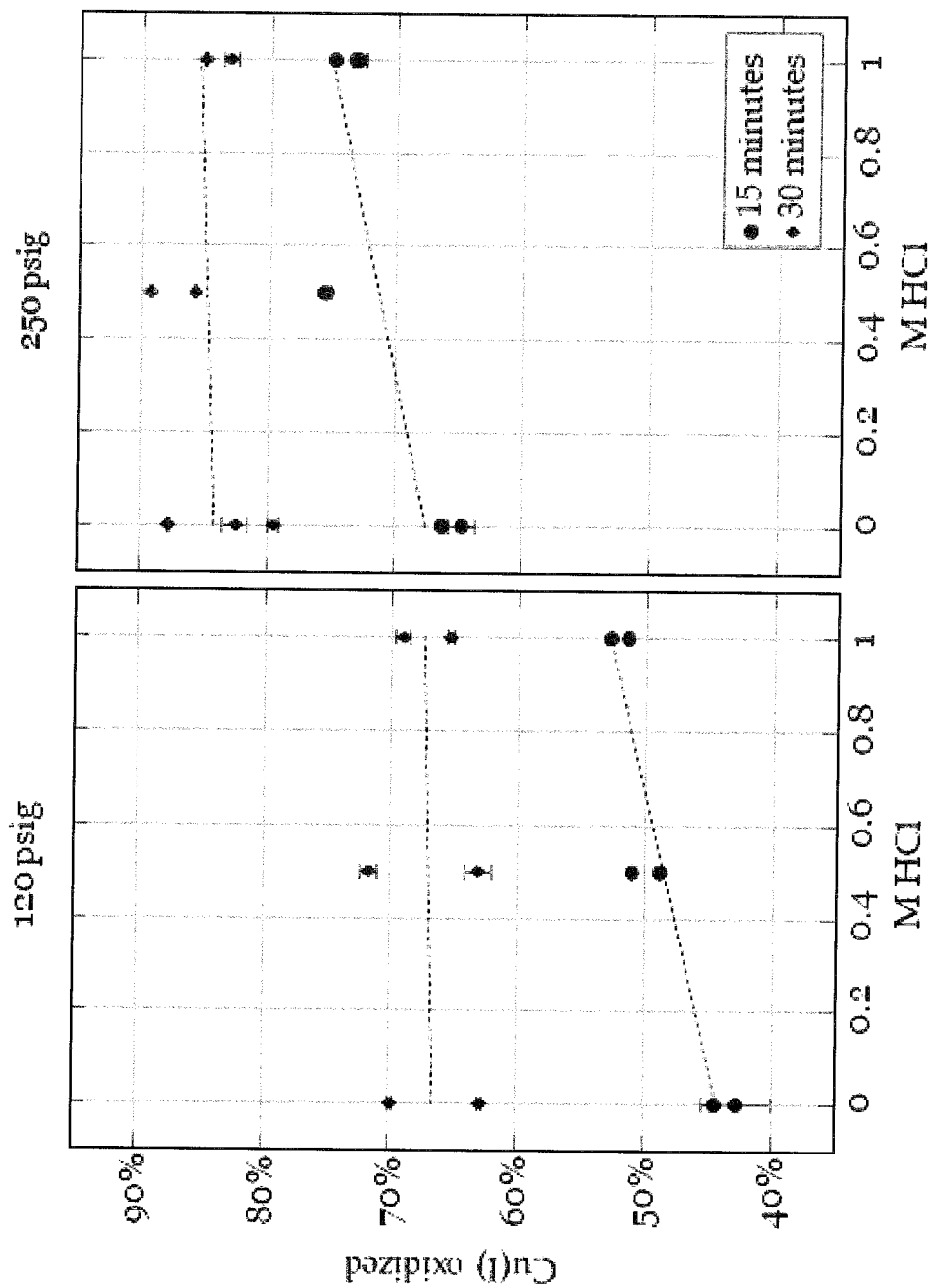
FIG. 7 is a graph illustrating effects of the oxidant concentrations and pressure on the oxychlorination reaction, as described in Example 4.

As shown in FIG. 7, after reaction times of 15 minutes, the samples showed an increased conversion of Cu(I) to Cu(II) with higher HCl concentrations. After a reaction time of 30 minutes though, this difference leveled out for this anolyte concentration, however, the conversion of Cu(I) to Cu(II) increased between individual samples. Also can be seen in FIG. 7 that an increase in the oxygen partial pressure from 120 psig to 250 psig at 100° C. temperature, increased both reaction speed and reaction endpoint.

Figure 8:
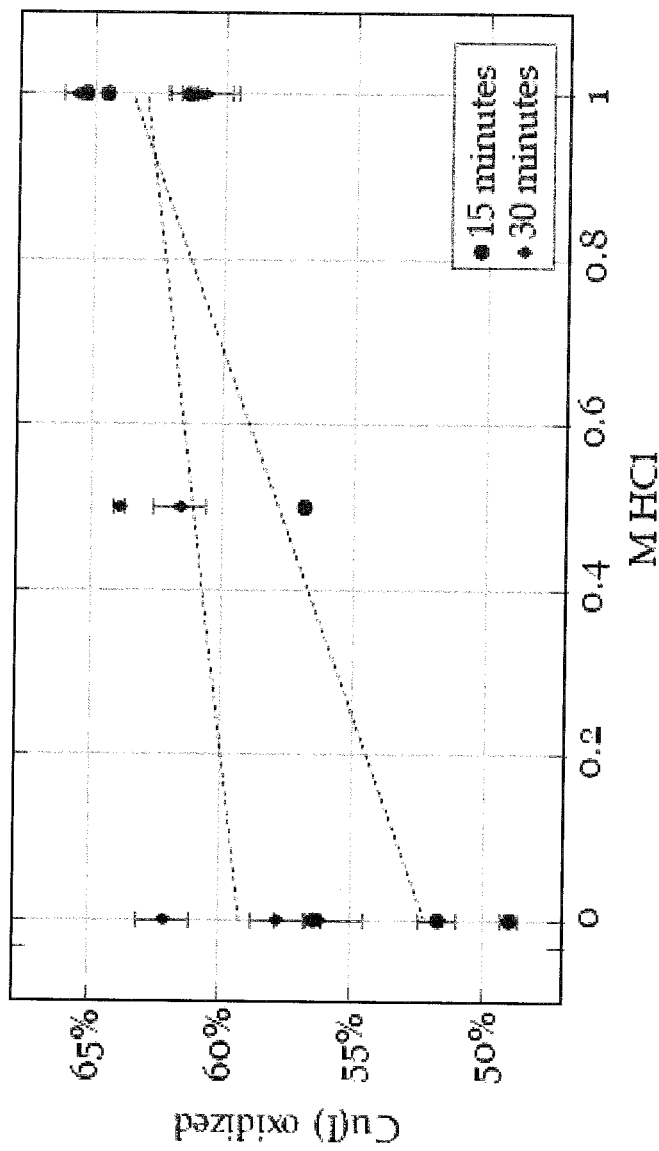
FIG. 8 is a graph illustrating effects of temperature on the oxychlorination reaction, as described in Example 4.

The temperature effect was also observed, as shown in FIG. 8. Higher temperature of 150° C. compared to 100° C. above (at 120 psig), increased the reaction speed.

What is claimed is:

1. A method, comprising:
   (i) contacting an anode with an anode electrolyte in an electrochemical cell wherein the anode electrolyte comprises metal chloride and saltwater; contacting a cathode with a cathode electrolyte in the electrochemical cell; applying voltage to the anode and the cathode and oxidizing the metal chloride with metal ion in a lower oxidation state to a higher oxidation state at the anode;
   (ii) withdrawing the anode electrolyte from the electrochemical cell and chlorinating propylene with the anode electrolyte comprising the metal chloride with the metal ion in the higher oxidation state in the saltwater to result in one or more products comprising propylene chlorohydrin (PCH) and 1,2-dichloropropane (DCP) and the metal chloride with the metal ion in the lower oxidation state; or withdrawing the anode electrolyte from the electrochemical cell and chlorinating ethylene with the anode electrolyte comprising the metal chloride with the metal ion in the higher oxidation state in the saltwater to result in one or more products comprising chloroethanol (CE) and ethylene dichloride (EDC) and the metal chloride with the metal ion in the lower oxidation state;
   (iii) separating the one or more products comprising PCH and DCP or separating the one or more products comprising CE and EDC from the saltwater;
   (iv) hydrolyzing the DCP to the PCH in the one or more products comprising PCH and DCP or hydrolyzing the EDC to the CE in the one or more products comprising CE and EDC; and
   (v) epoxidizing the one or more products comprising PCH and DCP or the one or more products comprising CE and EDC with a base to form propylene oxide (PO) or ethylene oxide (EO), respectively.

2. The method of claim 1, further comprising oxychlorinating the metal chloride with the metal ion in the lower oxidation state in the saltwater after step (ii) and/or step (iii) to the metal ion in the higher oxidation state in presence of HCl and oxygen.

3. The method of claim 2, further comprising recirculating the metal chloride with the metal ion in the higher oxidation state back to step (ii).

4. The method of claim 1, wherein the chlorination results in between 20-90 wt % yield of PCH or between 20-90 wt % yield of CE.

5. The method of claim 1, further comprising forming sodium hydroxide in the cathode electrolyte and using the sodium hydroxide as the base to form the propylene oxide or the ethylene oxide.

6. The method of claim 1, wherein the one or more products from propylene or ethylene further comprise hydrochloric acid (HCl).

7. The method of claim 6, further comprising forming sodium hydroxide in the cathode electrolyte and using the sodium hydroxide to neutralize the HCl.

8. The method of claim 2, wherein the oxidizing, the chlorinating and the oxychlorinating steps are carried out in saltwater.

9. The method of claim 1, wherein the saltwater comprises alkali metal chloride.

10. The method of claim 9, wherein the alkali metal chloride is sodium chloride or potassium chloride.

11. The method of claim 2, wherein concentration of the metal chloride with the metal ion in the lower oxidation state entering the oxychlorination reaction is between about 0.5-2M; concentration of the metal chloride with the metal ion in the lower oxidation state entering the chlorination reaction is between about 0.1-1.8M; concentration of the metal chloride with the metal ion in the lower oxidation state entering the electrochemical reaction is between about 0.6-2.5M; or combinations thereof.

12. The method of claim 2, further comprising separating the metal chloride solution from the one or more products comprising PCH or the CE after the chlorinating step and delivering the metal chloride solution back to the electrochemical reaction and/or the oxychlorination reaction.

13. The method of claim 1, wherein yield of the PO or yield of the EO is more than 90 wt % and/or space time yield (STY) of the PO or STY of the EO is more than 0.1.

14. The method of claim 1, wherein the metal chloride with the metal ion in the lower oxidation state is CuCl and the metal chloride with the metal ion in the higher oxidation state is $CuCl_2$.

15. A system, comprising:
an electrochemical cell comprising an anode in contact with an anode electrolyte wherein the anode electrolyte comprises metal chloride and saltwater; a cathode in contact with a cathode electrolyte; and a voltage source configured to apply voltage to the anode and the cathode wherein the anode is configured to oxidize the metal chloride with the metal ion from a lower oxidation state to a higher oxidation state; and/or an oxychlorination reactor operably connected to the electrochemical cell and/or chlorination reactor and configured to oxychlorinate the metal chloride with the metal ion from the lower oxidation state to the higher oxidation state in presence of HCl and oxygen;

a chlorination reactor operably connected to the electrochemical cell and/or the oxychlorination reactor wherein the chlorination reactor is configured to receive the metal chloride with the metal ion in the higher oxidation state from the electrochemical cell and/or configured to receive the metal chloride solution with the metal ion in the higher oxidation state from the oxychlorination reactor and chlorinate propylene or ethylene with the metal chloride with the metal ion in the higher oxidation state to result in one or more products comprising PCH and DCP or one or more products comprising CE and EDC, respectively, and the metal chloride solution with the metal ion in the lower oxidation state;

a separator operably connected to the chlorination reactor and configured to separate the one or more products comprising PCH and DCP or the one or more products comprising CE and EDC from the metal chloride solution in the saltwater;

a hydrolyzing chamber operably connected to the separator and configured to receive the one or more products comprising PCH and DCP or the one or more products comprising CE and EDC from the separator and hydrolyze the DCP to the PCH or hydrolyze the DCE to the CE; and an epoxide reactor operably connected to the hydrolyzing chamber and configured to epoxidize the one or more products comprising PCH and DCP or the one or more products comprising CE and EDC with a base to form PO or EO, respectively.

16. The system of claim 15, wherein the electrochemical cell, the chlorination reactor and the oxychlorination reactor are all configured to carry out the reactions in saltwater.

* * * * *